US010973978B2

(12) United States Patent
Nazzaro et al.

(10) Patent No.: US 10,973,978 B2
(45) Date of Patent: Apr. 13, 2021

(54) FLUID FLOW REGULATION ARRANGEMENTS FOR DRUG DELIVERY DEVICES

(71) Applicant: Insulet Corporation, Acton, MA (US)

(72) Inventors: David Nazzaro, Groveland, MA (US); Ian McLaughlin, Boxboro, MA (US); Daniel Allis, Boxford, MA (US); Jason O'Connor, Acton, MA (US)

(73) Assignee: INSULET CORPORATION, Acton, MA (US)

( * ) Notice: Subject to any disclaimer, the term of this patent is extended or adjusted under 35 U.S.C. 154(b) by 180 days.

(21) Appl. No.: 16/049,388

(22) Filed: Jul. 30, 2018

(65) Prior Publication Data

US 2019/0038835 A1 Feb. 7, 2019

Related U.S. Application Data

(60) Provisional application No. 62/540,947, filed on Aug. 3, 2017.

(51) Int. Cl.
*A61M 5/168* (2006.01)
*A61M 5/28* (2006.01)
(Continued)

(52) U.S. Cl.
CPC .... *A61M 5/16877* (2013.01); *A61M 5/16804* (2013.01); *A61M 5/16813* (2013.01);
(Continued)

(58) Field of Classification Search
CPC .............. A61M 5/168; A61M 5/16804; A61M 5/16813; A61M 5/16877; A61M 5/16881;
(Continued)

(56) References Cited

U.S. PATENT DOCUMENTS 1,441,508 A 1/1923 Marius et al.
2,198,666 A 4/1940 Gruskin
(Continued)

FOREIGN PATENT DOCUMENTS

CA 606281 A 10/1960
CN 1375338 A 10/2002
(Continued)

OTHER PUBLICATIONS

European Search Report and Written Opinion for the European Patent Application No. EP19177571, dated Oct. 30, 2019, 8 pages.
(Continued)

*Primary Examiner* — Nathan R Price
*Assistant Examiner* — Anna E Goldberg-Richmeier
(74) *Attorney, Agent, or Firm* — Kacvinsky Daisak Bluni PLLC

(57) ABSTRACT

A fluid flow regulator of a fluid delivery system that can adjust a flow rate of a liquid drug dispensed from a liquid drug container to a user is provided. The fluid flow regulator can be coupled to an end of the liquid drug container. The fluid flow regulator can include a compliance plate and a flow channel selector plate having a fluid flow channel. The flow channel selector plate can be rotated relative to the compliance plate and the liquid drug container to expose a selected portion of the fluid flow channel to openings in the compliance plate that are in fluid communication with the liquid drug stored in the liquid drug container. The selected portion of the fluid flow channel can correspond to a
(Continued)

corresponding flow resistance of the liquid drug through the fluid flow channel, thereby regulating the flow of the liquid drug to the user.

18 Claims, 25 Drawing Sheets

(51) Int. Cl.
  *A61M 5/32* (2006.01)
  *A61M 5/315* (2006.01)
(52) U.S. Cl.
  CPC ........ *A61M 5/16854* (2013.01); *A61M 5/281* (2013.01); *A61M 5/31553* (2013.01); *A61M 5/32* (2013.01); *A61M 2205/123* (2013.01); *A61M 2205/3334* (2013.01); *A61M 2206/14* (2013.01); *A61M 2206/20* (2013.01)
(58) Field of Classification Search
  CPC .............. A61M 5/141; A61M 5/31553; A61M 5/1408; A61M 5/16827; A61M 2205/3334; A61M 2205/3337
  See application file for complete search history.

(56) References Cited

U.S. PATENT DOCUMENTS

| | | |
|---|---|---|
| 3,176,712 A | 4/1965 | Ramsden |
| 3,297,260 A | 1/1967 | Barlow |
| 3,464,359 A | 9/1969 | King |
| 3,885,662 A | 5/1975 | Schaefer |
| 3,946,732 A | 3/1976 | Hurscham |
| 3,947,692 A | 3/1976 | Payne |
| 3,993,061 A | 11/1976 | OLeary |
| 4,108,177 A | 8/1978 | Pistor |
| 4,152,098 A | 5/1979 | Moody et al. |
| 4,210,173 A | 7/1980 | Choksi et al. |
| 4,221,219 A | 9/1980 | Tucker |
| 4,257,324 A | 3/1981 | Stefansson et al. |
| 4,268,150 A | 5/1981 | Chen |
| 4,313,439 A | 2/1982 | Babb et al. |
| 4,371,790 A | 2/1983 | Manning et al. |
| 4,417,889 A | 11/1983 | Choi |
| 4,424,720 A | 1/1984 | Bucchianeri |
| 4,435,173 A | 3/1984 | Siposs et al. |
| 4,498,843 A | 2/1985 | Schneider et al. |
| 4,507,115 A | 3/1985 | Kambara et al. |
| 4,551,134 A | 11/1985 | Slavik et al. |
| 4,562,751 A | 1/1986 | Nason et al. |
| 4,567,549 A | 1/1986 | Lemme |
| 4,585,439 A | 4/1986 | Michel |
| 4,601,707 A | 7/1986 | Albisser et al. |
| 4,634,427 A | 1/1987 | Hannula et al. |
| 4,671,429 A | 6/1987 | Spaanderman et al. |
| 4,678,408 A | 7/1987 | Nason et al. |
| 4,684,368 A | 8/1987 | Kenyon |
| 4,685,903 A | 8/1987 | Cable et al. |
| 4,755,169 A | 7/1988 | Sarnoff et al. |
| 4,766,889 A | 8/1988 | Trick et al. |
| 4,808,161 A | 2/1989 | Kamen |
| 4,846,797 A | 7/1989 | Howson et al. |
| 4,858,619 A | 8/1989 | Toth |
| 4,898,579 A | 2/1990 | Groshong et al. |
| 4,908,017 A | 3/1990 | Howson et al. |
| 4,944,659 A | 7/1990 | Labbe et al. |
| 4,969,874 A | 11/1990 | Michel et al. |
| 5,007,458 A | 4/1991 | Marcus et al. |
| 5,020,325 A | 6/1991 | Henault |
| 5,062,841 A | 11/1991 | Siegel |
| 5,147,311 A * | 9/1992 | Pickhard ............... A61M 5/148 604/131 |
| 5,178,609 A | 1/1993 | Ishikawa |
| 5,205,819 A | 4/1993 | Ross et al. |
| 5,213,483 A | 5/1993 | Flaherty et al. |
| 5,222,362 A | 6/1993 | Maus et al. |
| 5,236,416 A | 8/1993 | McDaniel et al. |
| 5,261,882 A | 11/1993 | Sealfon |
| 5,261,884 A | 11/1993 | Stern et al. |
| 5,277,338 A | 1/1994 | Divall |
| 5,281,202 A | 1/1994 | Weber et al. |
| 5,346,476 A | 9/1994 | Elson |
| 5,364,342 A | 11/1994 | Beuchat et al. |
| 5,388,615 A | 2/1995 | Edlund et al. |
| 5,433,710 A | 7/1995 | VanAntwerp et al. |
| 5,503,628 A | 4/1996 | Fetters et al. |
| 5,520,661 A | 5/1996 | Lal et al. |
| 5,533,389 A | 7/1996 | Kamen et al. |
| 5,582,593 A | 12/1996 | Hultman |
| 5,618,269 A | 4/1997 | Jacobsen et al. |
| 5,637,095 A | 6/1997 | Nason et al. |
| 5,665,070 A | 9/1997 | McPhee |
| 5,713,875 A | 2/1998 | Tanner, II |
| 5,747,350 A | 5/1998 | Sattler |
| 5,748,827 A | 5/1998 | Holl et al. |
| 5,776,103 A | 7/1998 | Kriesel et al. |
| 5,779,676 A | 7/1998 | Kriesel et al. |
| 5,785,688 A | 7/1998 | Joshi et al. |
| 5,797,881 A | 8/1998 | Gadot |
| 5,800,397 A | 9/1998 | Wilson et al. |
| 5,807,075 A | 9/1998 | Jacobsen et al. |
| 5,839,467 A | 11/1998 | Saaski et al. |
| 5,891,097 A | 4/1999 | Saito et al. |
| 5,897,530 A | 4/1999 | Jackson |
| 5,906,597 A | 5/1999 | McPhee |
| 5,911,716 A | 6/1999 | Rake et al. |
| 5,919,167 A | 7/1999 | Mulhauser et al. |
| 5,957,890 A | 9/1999 | Mann et al. |
| 5,961,492 A | 10/1999 | Kriesel et al. |
| 5,971,963 A | 10/1999 | Choi |
| 6,019,747 A | 2/2000 | McPhee |
| 6,050,457 A | 4/2000 | Arnold et al. |
| 6,068,615 A | 5/2000 | Brown et al. |
| 6,086,615 A | 7/2000 | Wood et al. |
| 6,159,188 A | 12/2000 | Laibovitz et al. |
| 6,174,300 B1 | 1/2001 | Kriesel et al. |
| 6,190,359 B1 | 2/2001 | Heruth |
| 6,200,293 B1 | 3/2001 | Kriesel et al. |
| 6,352,522 B1 * | 3/2002 | Kim ........................ A61M 5/28 604/201 |
| 6,363,609 B1 | 4/2002 | Pickren |
| 6,375,638 B2 | 4/2002 | Nason et al. |
| 6,474,219 B2 | 11/2002 | Klitmose et al. |
| 6,485,461 B1 | 11/2002 | Mason et al. |
| 6,485,462 B1 | 11/2002 | Kriesel |
| 6,488,652 B1 | 12/2002 | Weijand et al. |
| 6,520,936 B1 | 2/2003 | Mann |
| 6,527,744 B1 | 3/2003 | Kriesel et al. |
| 6,537,249 B2 | 3/2003 | Kriesel et al. |
| 6,539,286 B1 | 3/2003 | Jiang |
| 6,569,115 B1 | 5/2003 | Barker et al. |
| 6,595,956 B1 | 7/2003 | Gross et al. |
| 6,656,158 B2 | 12/2003 | Mahoney et al. |
| 6,699,218 B2 | 3/2004 | Flaherty et al. |
| 6,723,072 B2 | 4/2004 | Flaherty et al. |
| 6,749,407 B2 | 6/2004 | Xie et al. |
| 6,851,260 B2 | 2/2005 | Merno |
| 6,883,778 B1 | 4/2005 | Newton et al. |
| 7,018,360 B2 | 3/2006 | Flaherty et al. |
| 7,104,275 B2 * | 9/2006 | Dille ..................... F16K 7/045 137/487.5 |
| 7,128,727 B2 | 10/2006 | Flaherty et al. |
| 7,144,384 B2 | 12/2006 | Gorman et al. |
| 7,160,272 B1 | 1/2007 | Eyal et al. |
| 7,771,392 B2 | 8/2010 | De Polo et al. |
| 7,914,499 B2 | 3/2011 | Gonnelli et al. |
| 8,382,703 B1 | 2/2013 | Abdelaal |
| 8,499,913 B2 | 8/2013 | Gunter |
| 8,939,935 B2 | 1/2015 | O'Connor et al. |
| 9,180,244 B2 | 11/2015 | Anderson et al. |
| 9,192,716 B2 | 11/2015 | Jugl et al. |
| 9,402,950 B2 | 8/2016 | Dilanni et al. |
| 9,539,596 B2 | 1/2017 | Ikushima |
| 2001/0016710 A1 | 8/2001 | Nason et al. |

(56) References Cited

U.S. PATENT DOCUMENTS

| | | |
|---|---|---|
| 2001/0056258 A1 | 12/2001 | Evans |
| 2002/0029018 A1 | 3/2002 | Jeffrey |
| 2002/0032374 A1 | 3/2002 | Holker |
| 2002/0037221 A1 | 3/2002 | Mastrangelo |
| 2002/0173769 A1 | 11/2002 | Gray et al. |
| 2002/0173830 A1 | 11/2002 | Starkweather |
| 2003/0040715 A1 | 2/2003 | D'Antonio et al. |
| 2003/0097092 A1 | 5/2003 | Flaherty |
| 2003/0163097 A1 | 8/2003 | Fleury |
| 2003/0199825 A1 | 10/2003 | Flaherty |
| 2004/0010207 A1 | 1/2004 | Flaherty |
| 2004/0064088 A1 | 4/2004 | Gorman et al. |
| 2004/0068224 A1 | 4/2004 | Couvillon et al. |
| 2004/0069044 A1 | 4/2004 | Lavi et al. |
| 2004/0092865 A1 | 5/2004 | Flaherty |
| 2004/0094733 A1 | 5/2004 | Hower |
| 2004/0153032 A1 | 8/2004 | Garribotto |
| 2005/0020980 A1 | 1/2005 | Inoue et al. |
| 2005/0165363 A1 | 7/2005 | Judson et al. |
| 2005/0203461 A1 | 9/2005 | Flaherty et al. |
| 2005/0238507 A1 | 10/2005 | Dilanni et al. |
| 2005/0273059 A1 | 12/2005 | Mernoe et al. |
| 2005/0277882 A1* | 12/2005 | Kriesel ............. A61M 5/14244 604/131 |
| 2006/0041229 A1 | 2/2006 | Garibotto et al. |
| 2006/0079765 A1 | 4/2006 | Neer et al. |
| 2006/0155210 A1 | 7/2006 | Beckman et al. |
| 2006/0173439 A1 | 8/2006 | Thorne et al. |
| 2006/0178633 A1 | 8/2006 | Garibotto et al. |
| 2006/0253085 A1 | 11/2006 | Geismar et al. |
| 2006/0282290 A1 | 12/2006 | Flaherty et al. |
| 2007/0005018 A1 | 1/2007 | Tekbuchava |
| 2007/0118405 A1 | 5/2007 | Campbell et al. |
| 2007/0282269 A1 | 12/2007 | Carter et al. |
| 2008/0004515 A1 | 1/2008 | Jennewine |
| 2008/0051738 A1 | 2/2008 | Griffin |
| 2008/0114304 A1 | 5/2008 | Nalesso et al. |
| 2008/0172028 A1 | 7/2008 | Blomquist |
| 2008/0294040 A1 | 11/2008 | Mohiuddin et al. |
| 2009/0024083 A1 | 1/2009 | Kriesel et al. |
| 2009/0062767 A1 | 3/2009 | Van Antwerp et al. |
| 2009/0198215 A1 | 8/2009 | Chong et al. |
| 2009/0278875 A1 | 11/2009 | Holm et al. |
| 2010/0036326 A1 | 2/2010 | Matusch |
| 2010/0152658 A1 | 6/2010 | Hanson et al. |
| 2010/0241066 A1 | 9/2010 | Hansen et al. |
| 2011/0054399 A1 | 3/2011 | Chong et al. |
| 2011/0144586 A1 | 6/2011 | Michaud et al. |
| 2011/0230833 A1 | 9/2011 | Landman et al. |
| 2012/0078161 A1 | 3/2012 | Masterson et al. |
| 2013/0006213 A1 | 1/2013 | Arnitz et al. |
| 2013/0017099 A1 | 1/2013 | Genoud et al. |
| 2013/0177455 A1 | 7/2013 | Kamen et al. |
| 2013/0178803 A1 | 7/2013 | Raab |
| 2013/0245545 A1 | 9/2013 | Arnold et al. |
| 2013/0267932 A1 | 10/2013 | Franke et al. |
| 2014/0018730 A1 | 1/2014 | Muller-Pathle |
| 2014/0127048 A1 | 5/2014 | Dilanni et al. |
| 2014/0128839 A1 | 5/2014 | Dilanni et al. |
| 2014/0142508 A1 | 5/2014 | Dilanni et al. |
| 2014/0148784 A1 | 5/2014 | Anderson et al. |
| 2014/0171901 A1 | 6/2014 | Langsdorf et al. |
| 2015/0041498 A1 | 2/2015 | Kakiuchi et al. |
| 2015/0064036 A1 | 3/2015 | Eberhard |
| 2015/0137017 A1* | 5/2015 | Ambrosina ........... B23P 15/001 251/208 |
| 2015/0202386 A1 | 7/2015 | Brady et al. |
| 2015/0290389 A1 | 10/2015 | Nessel |
| 2015/0297825 A1 | 10/2015 | Focht et al. |
| 2016/0008549 A1 | 1/2016 | Plumptre et al. |
| 2016/0025544 A1 | 1/2016 | Kamen et al. |
| 2016/0082242 A1* | 3/2016 | Burton ............. A61M 5/14248 604/506 |
| 2016/0193423 A1 | 7/2016 | Bilton |
| 2017/0021096 A1 | 1/2017 | Cole et al. |
| 2017/0021137 A1 | 1/2017 | Cole |
| 2017/0100541 A1* | 4/2017 | Constantineau .... A61M 5/3271 |
| 2017/0216516 A1 | 8/2017 | Dale et al. |
| 2017/0239415 A1 | 8/2017 | Hwang et al. |
| 2018/0021521 A1 | 1/2018 | Sanchez |
| 2018/0313346 A1 | 11/2018 | Oakes et al. |
| 2019/0192782 A1 | 6/2019 | Pedersen et al. |
| 2019/0365993 A1 | 12/2019 | Staub et al. |

FOREIGN PATENT DOCUMENTS

| | | |
|---|---|---|
| DE | 4200595 A1 | 7/1993 |
| DE | 19723648 C1 | 8/1998 |
| EP | 0454331 A1 | 10/1991 |
| EP | 0789146 A1 | 8/1997 |
| EP | 0867196 A2 | 9/1998 |
| EP | 1065378 A2 | 1/2001 |
| EP | 1177802 A1 | 2/2002 |
| EP | 1403519 A1 | 3/2004 |
| EP | 2397181 A1 | 12/2011 |
| EP | 2468338 A1 | 6/2012 |
| EP | 2703024 A1 | 3/2014 |
| EP | 2830499 A1 | 2/2015 |
| FR | 2096275 A5 | 2/1972 |
| FR | 2455269 A1 | 11/1980 |
| FR | 2507637 A1 | 12/1982 |
| FR | 2731475 A1 | 9/1996 |
| GB | 357139 A | 9/1931 |
| GB | 810488 A | 3/1959 |
| GB | 875034 A | 8/1961 |
| GB | 1204836 A | 9/1970 |
| GB | 2008806 A | 6/1979 |
| GB | 2077367 A | 12/1981 |
| GB | 2456681 A | 7/2009 |
| GB | 2549750 A | 11/2017 |
| IL | 46017 A | 11/1977 |
| JP | 06063133 A | 3/1994 |
| JP | 6098988 B2 | 4/1994 |
| JP | H06296690 A | 10/1994 |
| JP | H08238324 A | 9/1996 |
| JP | 2004247271 A | 9/2004 |
| JP | 2004274719 A | 9/2004 |
| JP | 2005188355 A | 7/2005 |
| JP | 2006159228 A | 6/2006 |
| JP | 2006249130 A | 9/2006 |
| NL | 1019126 C1 | 4/2003 |
| WO | 8101658 A1 | 6/1981 |
| WO | 8606796 A1 | 11/1986 |
| WO | 9415660 A1 | 7/1994 |
| WO | 9855073 A1 | 12/1998 |
| WO | 9856293 A1 | 12/1998 |
| WO | 9910040 A1 | 3/1999 |
| WO | 9910049 A1 | 3/1999 |
| WO | 9962576 A1 | 12/1999 |
| WO | 0029047 A1 | 5/2000 |
| WO | 0178812 A1 | 10/2001 |
| WO | 0220073 A2 | 3/2002 |
| WO | 2002026282 A2 | 4/2002 |
| WO | 02068823 A1 | 9/2002 |
| WO | 2002076535 A1 | 10/2002 |
| WO | 2003097133 A1 | 11/2003 |
| WO | 2004056412 A2 | 7/2004 |
| WO | 2004110526 A1 | 12/2004 |
| WO | 2007066152 A2 | 6/2007 |
| WO | 2008133702 A1 | 11/2008 |
| WO | 2009039203 A2 | 3/2009 |
| WO | 2009141005 A1 | 11/2009 |
| WO | 2010139793 A1 | 12/2010 |
| WO | 2011010198 A1 | 1/2011 |
| WO | 2011075042 A1 | 6/2011 |
| WO | 2011133823 A1 | 10/2011 |
| WO | 2012073032 A1 | 6/2012 |
| WO | 2013050535 A2 | 4/2013 |
| WO | 2013137893 A1 | 9/2013 |
| WO | 2014149357 A1 | 9/2014 |
| WO | 2015032772 A1 | 3/2015 |
| WO | 2015081337 A2 | 6/2015 |
| WO | 2015117854 A1 | 8/2015 |
| WO | 2015167201 A1 | 11/2015 |

(56) References Cited

FOREIGN PATENT DOCUMENTS

| WO | 2015177082 A1 | 11/2015 |
|---|---|---|
| WO | 2017148855 A1 | 9/2017 |
| WO | 2017187177 A1 | 11/2017 |

OTHER PUBLICATIONS

International Search Report and Written Opinion for the International Patent Application No. PCT/US2019/035756, dated Jul. 31, 2019, 11 pages.
International Preliminary Report on Patentability for the International Patent Application No. PCT/US18/14351, dated Jul. 23, 2019, 6 pages.
International Preliminary Report on Patentability for International application No. PCT/US2017/034811 dated Nov. 27, 2018 10 pages.
International Preliminary Report on Patentability for the International Patent Application No. PCT/US2017/046508 dated Feb. 12, 2019 10 pp.
International Preliminary Report on Patentability for the International Patent Application No. PCT/US2017/046777, dated Feb. 19, 2019, 8 pages.
International Preliminary Report on Patentability for the International Patent Application No. PCT/US2017/046737, dated Feb. 19, 2019, 8 pages.
International Preliminary Report on Patentability for the International Patent Application No. PCT/US2017/055054, dated Apr. 9, 2019, 8 pages.
International Search Report and Written Opinion for International application No. PCT/GB2007/004073, dated Jan. 31, 2008.
PCT International Search Report and Written Opinion dated Aug. 6, 2013, received in corresponding PCT Application No. PCT/US13/34674,pp. 1-19.
EPO Search Report dated Nov. 11, 2015, received in corresponding Application No. 13768938.6, 7 pgs.
International Search Report and Written Opinion for the International Patent Application No. PCT/US2019/063615, dated May 3, 2020, 16 pages.
International Preliminary Report on Patentability for the International Patent Application No. PCT/US2018/045155, dated Feb. 13, 2020, 10 pages.
Lind, et al.,"Linear Motion Miniature Actuators." Paper presented at the 2nd Tampere International Conference on Machine Automation, Tampere, Finland (Sep. 1998), 2 pages.

Author unknown, "The Animas R-1000 Insulin Pump—Animas Corporation intends to exit the insulin pump business and discontinue the manufacturing and sale of Animas® Vibe® and One Touch Ping® insulin pumps." [online], Dec. 1999 [retrieved on Jan. 8, 2019]. Retrieved from the Internet URL: http://www.animaspatientsupport.com/, 2 pages.
Author unknown, CeramTec "Discover the Electro Ceramic Products CeramTec acquired from Morgan Advanced Materials" [online], Mar. 1, 2001 [retrieved on Jan. 8, 2019. Retrieved from the Internet URL: http://www.morgantechnicalceramics.com/, 2 pages.
Vaughan, M.E., "The Design, Fabrication, and Modeling of a Piezoelectric Linear Motor." Master's thesis, Virginia Polytechnic Institute and State University, VA. (2001), 93 pages.
Galante, et al., "Design, Modeling, and Performance of a High Force Piezoelectric Inchworm Motor," Journal of Intelligent Material Systems and Structures, vol. 10, 962-972 (1999), 11 pages.
International Search Report and Written Opinion for International Application No. PCT/US2018/014351, dated Jun. 4, 2018, 9 pages.
International Search Report and Written Opinion for International Application No. PCT/US2017/055054, dated Jan. 25, 2018, 13 pages.
International Search Report and Written Opinion for International Application No. PCT/US2018/045155, dated Oct. 15, 2018, 15 pages.
International Search Report and Written Opinion for International Application No. PCT/US2017/034811, dated Oct. 18, 2017, 17 pages.
International Search Report and Written Opinion for International Application No. PCT/US2017/046508, dated Jan. 17, 2018, 14 pages.
International Search Report and Written Opinion for International Application No. PCT/US2017/034814, dated Oct. 11, 2017, 18 pages.
International Search Report and Written Opinion for International Application No. PCT/US2017/046777, dated Dec. 13, 2017, 14 pages.
International Search Report and Written Opinion for International Application No. PCT/US2017/046737, dated Dec. 14, 2017, 11 pages.
International Search Report and Written Opinion for Application No. PCT/US2019/059854, dated Aug. 26, 2020, 15 pages.
European Search Report for the European Patent Application No. EP20174878, dated Sep. 29, 2020, 3 pages.

\* cited by examiner

FLUID FLOW REGULATION ARRANGEMENTS FOR DRUG DELIVERY DEVICES

CROSS-REFERENCE TO RELATED APPLICATIONS

This application claims the benefit of U.S. Provisional Application No. 62/540,947, filed Aug. 3, 2017, which is incorporated herein by reference in its entirety.

TECHNICAL FIELD

The present application generally relates to medication delivery devices, and more particularly to systems and methods for regulating the flow of a liquid drug delivered by a drug delivery device.

BACKGROUND

Many conventional drug delivery systems are designed to be wearable and to deliver a drug slowly to the patient over time. Some conventional wearable drug delivery systems use spring arrangements to force a plunger to move within a liquid drug cartridge, expelling liquid drug from the cartridge into a needle that provides the drug to a patient. One issue with such spring-powered devices is that the force applied to the plunger generally decays as the spring expands. This spring force decay can cause variations in the flow rate at which the liquid drug is expelled from the liquid drug container, resulting in uneven delivery of drug to the user.

A need therefore exists for a drug delivery device that has improved flow control characteristics.

DETAILED DESCRIPTION

Figure 1A:
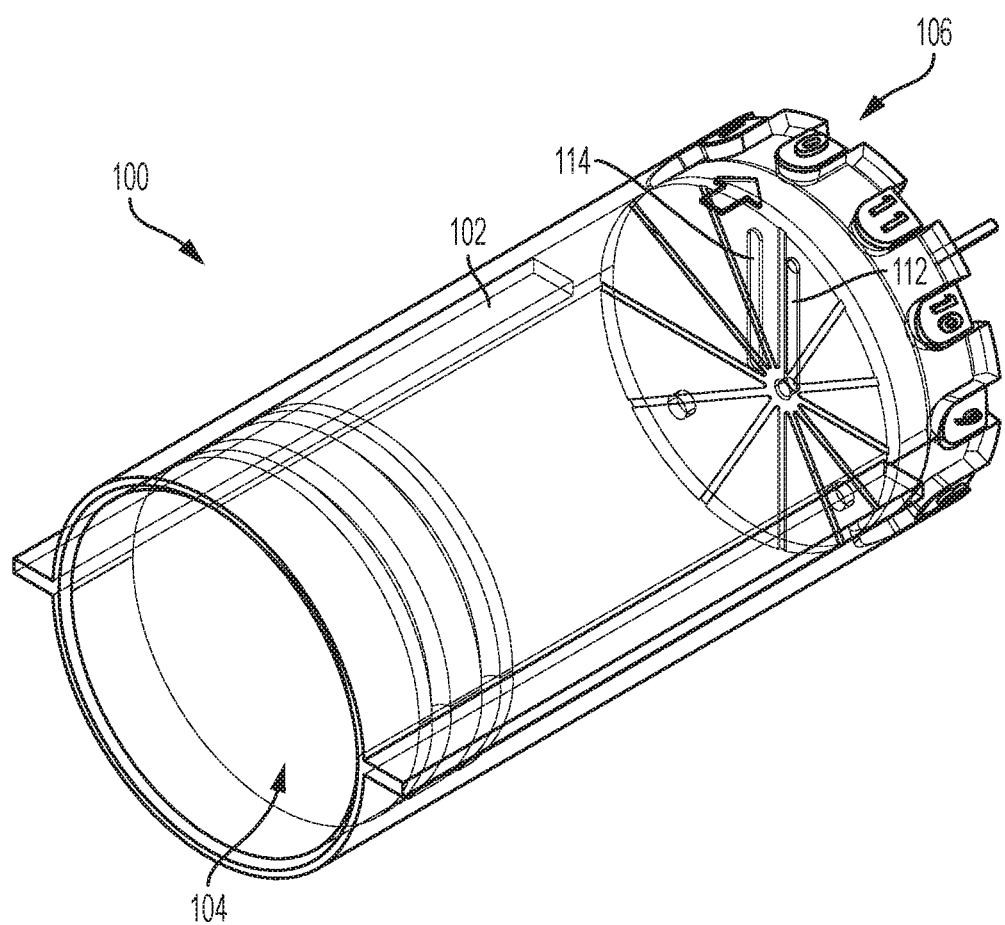
FIG. 1A illustrates an isometric view of a first exemplary drug delivery system.

This disclosure presents various systems, components, and methods related to drug delivery devices. Each of the systems, components, and methods disclosed herein provides one or more advantages over conventional systems, components, and methods.

Various embodiments include a fluid flow regulator of a fluid delivery system that can adjust a flow rate of a liquid drug dispensed from a liquid drug container to a user. The fluid flow regulator can be coupled to an end of the liquid drug container. The fluid flow regulator can include a compliance plate and a flow channel selector plate having a fluid flow channel. The flow channel selector plate can be rotated relative to the compliance plate and the liquid drug container to expose a selected portion of the fluid flow channel to openings in the compliance plate that are in fluid communication with the liquid drug stored in the liquid drug container. The selected portion of the fluid flow channel can correspond to a corresponding flow resistance of the liquid drug through the fluid flow channel, thereby regulating the flow of the liquid drug to the user.

In a wearable drug delivery system, it may be beneficial to regulate a rate of delivery of a drug administered or provided to the user. Thus, a fluid flow regulator may be integrated into a custom drug container or attached to a standard primary container. The fluid flow regulator can use a tapered channel of varying length to change the outlet flow rate. According to various embodiments, flow calculations can be developed using Poiseuille's Law:

$$Q = \frac{\pi P r^4}{8\eta l}$$

The disclosed fluid flow regulators can be used to regulate fluid exiting the drug delivery systems at finite and infinitely adjustable flow rates. According to various embodiments, laminar flow (e.g., Reynold's number sub 4000 for water) can be assumed. Disclosed arrangements can be advantageous because in some drug therapies it is desirous to meter out the drug to a patient at a steady rate (e.g., for basal flow or delivery). Steady basal rates become difficult to achieve when using a mechanical, stored energy drive source, like a spring. Springs are inexpensive drive sources that provide repeatable performance and can withstand long shelf life, large temperature variation, and abuse in drop scenarios, while still performing properly thereafter. Springs, however, will have a decaying force over extension (e.g., for a helical compression spring) spring constant or k. As force decays, drive pressure is reduced, and as a result the flow rate exiting the device is reduced. If outlet flow rate can be controlled, shorter and stiffer springs can be used to drive flow. Some of these springs may have a high k-value which means they lose drive force quickly and over a short stroke. The disclosed fluid regulators can accommodate the use of springs with relatively high k-value (and/or springs with any k-value including relatively low k-values).

The disclosed fluid flow regulators can be adjusted, so as the spring force reduces (e.g., over the length of its stroke), the flow path restriction is reduced to keep the flow of drug consistent. In some embodiments the configuration of the fluid flow regulator is fixed and not adjustable by a user. In some embodiments a plurality of discrete flow rate settings are provided. In one exemplary embodiment available settings are from a minimum value (e.g., off) to a maximum value (e.g., full flow). In some embodiments the configuration of the fluid flow regulator is adjustable by a user or can be automatically adjusted to provide a desired or set flow rate.

Figure 1B:
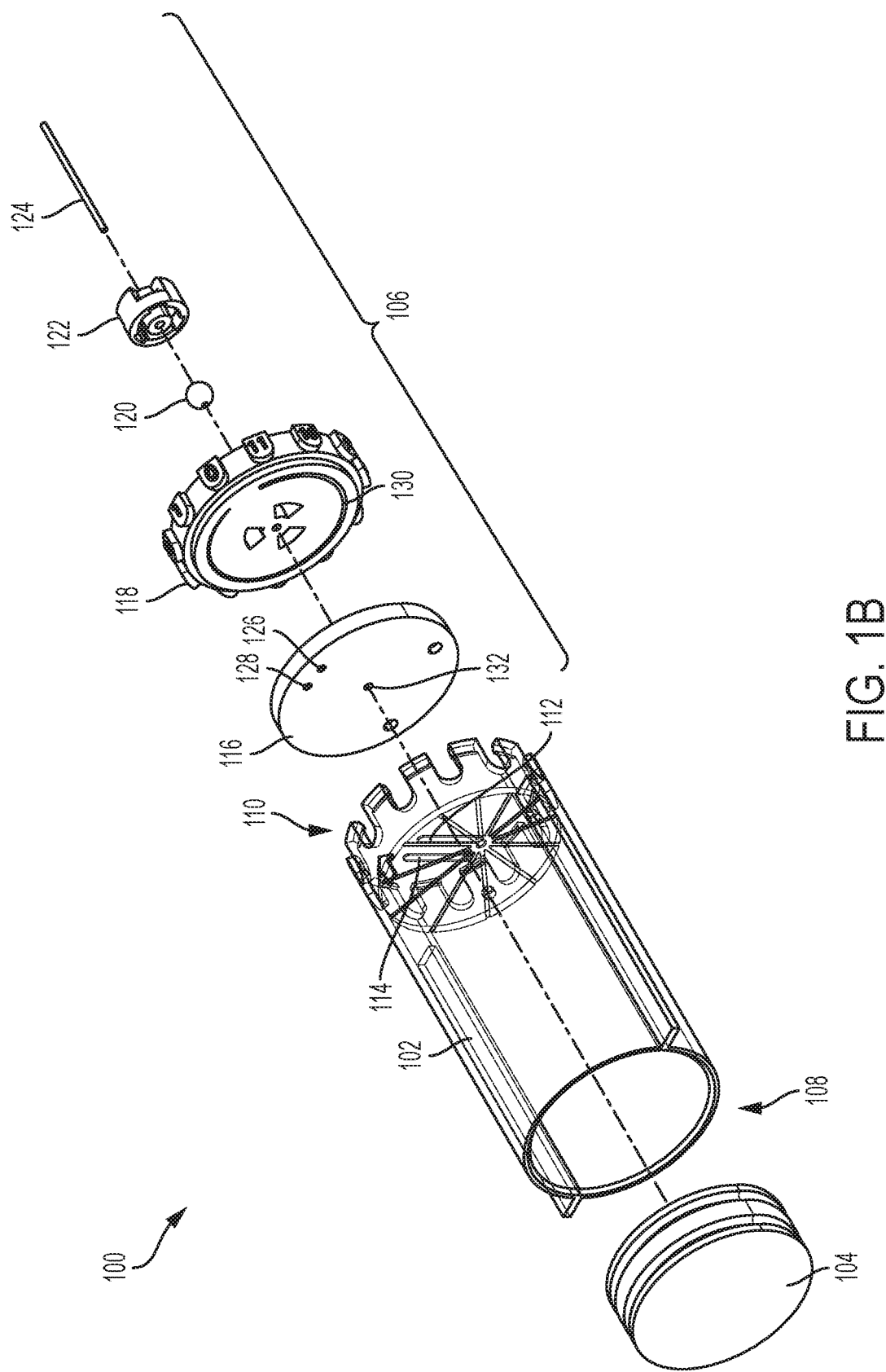
FIG. 1B illustrates an exploded view of the first exemplary drug system.

Referring to FIGS. 1A and 1B, a drug container system 100 (or liquid drug container system) is shown. FIG. 1A shows the drug container system 100 in an assembled state. FIG. 1B shows an exploded view of the drug container system 100 to illustrate the arrangement of the constituent components of the drug container system 100. The drug container system 100 can store or hold any liquid drug or any other fluid or therapeutic agent.

As shown in FIGS. 1A and 1B, the drug container system 100 can include a drug container 102 (or liquid drug container), a plunger 104, and a fluid flow regulator 106. The drug container 102 may be a generally cylindrical body and may receive the plunger 104 at a first end 108, and may receive the fluid flow regulator 106 (and/or components thereof) at an opposite, second, end 110. The drug container 102 can be of any size in shape. In various embodiments, the drug container 102 can be a custom-molded container and/or can have a custom shape. The second end 110 of the drug container 102 may include various features that interact with portions of the fluid flow regulator 106, as will be described. Specifically, the second end 110 of the drug container 102 may have an inlet recess or manifold 112 and an outlet recess or manifold 114 (see also FIG. 4 and related discussion) that are configured to enable flow to be directed to specific locations within the fluid flow regulator 106.

The fluid flow regulator 106 may include a compliance plate 116, a flow channel selector plate 118, a needle ball 120, a needle ball retainer 122, and a hard needle 124. The compliance plate 116 can be a flat elastomeric member or component that can seal the second end 110 of the drug container 102 from the flow channel selector plate 118. The compliance plate 116 can include first and second openings 126 and 128. The first and second openings 126 and 128 may fluidly couple to the first and second recesses 112 and 114, respectively (e.g., they may be in communication or fluid communication therewith, or coupled thereto). The arrangement of the first and second recesses 112 and 114 and the first and second openings 126 and 128 can direct fluid stored in the drug container 102 to flow to a fluid flow channel 130 disposed within (e.g., positioned on the flow channel selector plate 118 and/or coupled or attached thereto). The compliance plate 116 can also include a third opening 132 that can be coupled to the hard needle 124 (e.g., a central opening), described in more detail further herein. In various embodiments, the first and second openings 126 and 128 can be positioned a same distance from a center of the compliance plate 116 (e.g., a same radial distance from the third opening 132).

As will be described in greater detail below, by adjusting the position of the flow channel selector plate 118, the size, length, and/or configuration of the fluid flow channel 130 can be adjusted to thereby adjust the flow resistance within the fluid flow channel 130 (and/or provided by the fluid flow channel 130). In various embodiments, the position of the flow channel selector plate 118 can be adjusted by rotating the flow channel selector plate 118 relative to a stationary compliance plate 116 (and liquid drug container 102). This adjustment, in turn, can be used to adjust the flow rate of a liquid drug travelling through the fluid flow channel 130 and, in turn, out to the user (e.g., through the needle 124). In various embodiments, the liquid drug passing through the fluid flow channel 130 can be provided to the user by coupling the hard needle 124 (or other fluid path or fluid path component) to the user.

FIGS. 2A-2B and 3A-3B show end views of the fluid flow regulator 106 positioned within the drug container 102 (e.g., viewing in the compliance plate 116 from the needle 124) as well as corresponding detailed close up views of the first and second opening 126 and 128 in relation to the fluid flow channel 130.

Figure 2A:
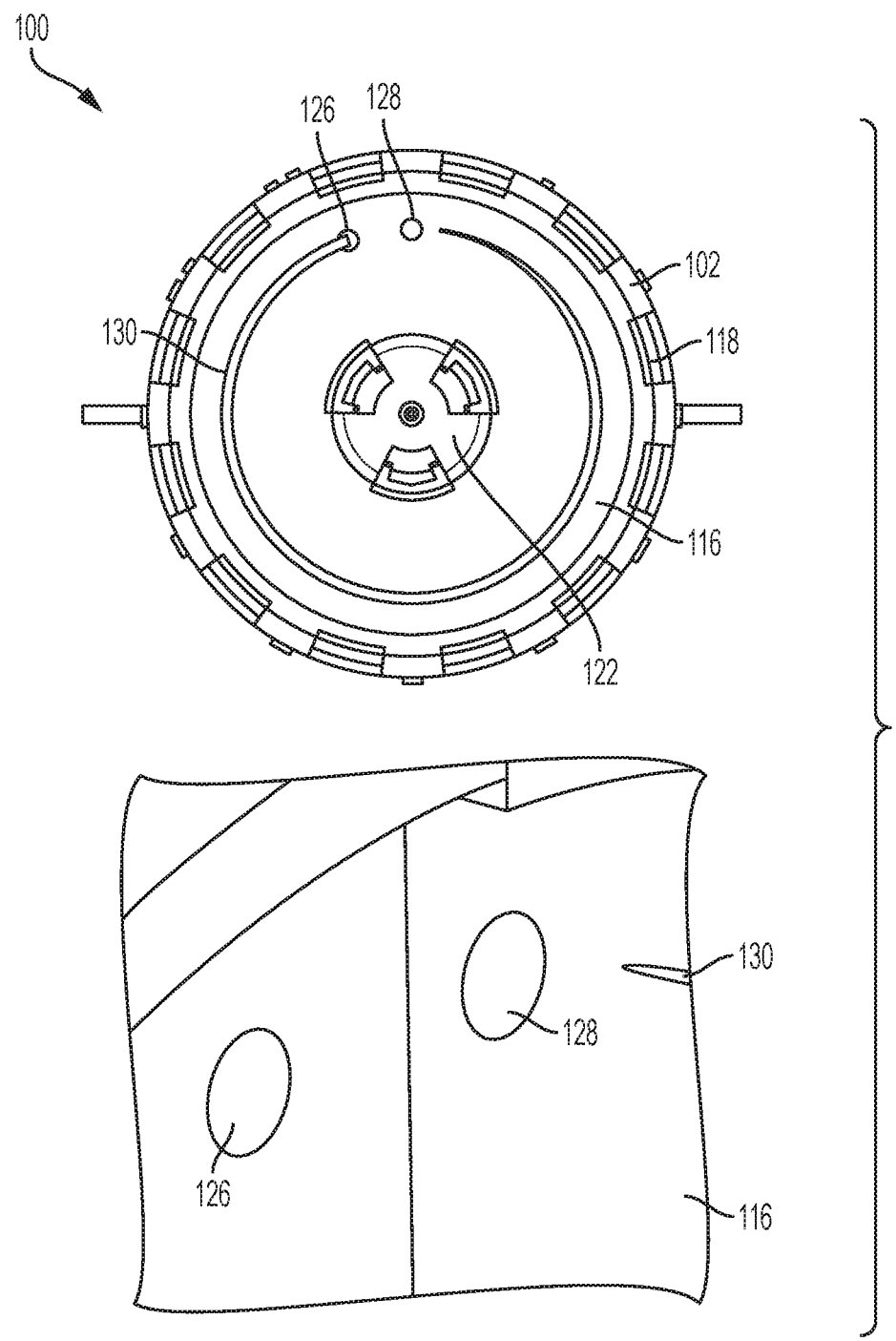
FIG. 2A illustrates an end view and a detail isometric view of an exemplary fluid flow regulator in a first operational state.

FIG. 2A shows the fluid flow regulator 106 in a minimum or a "0" position of the flow channel selector plate 118. In the "0" position, no part of the fluid flow channel 130 is coupled across the first and second openings 126 and 128 of the compliance plate 116. As such, flow is shut off and no liquid drug is expelled (or can flow) from the drug container 102.

Figure 2B:
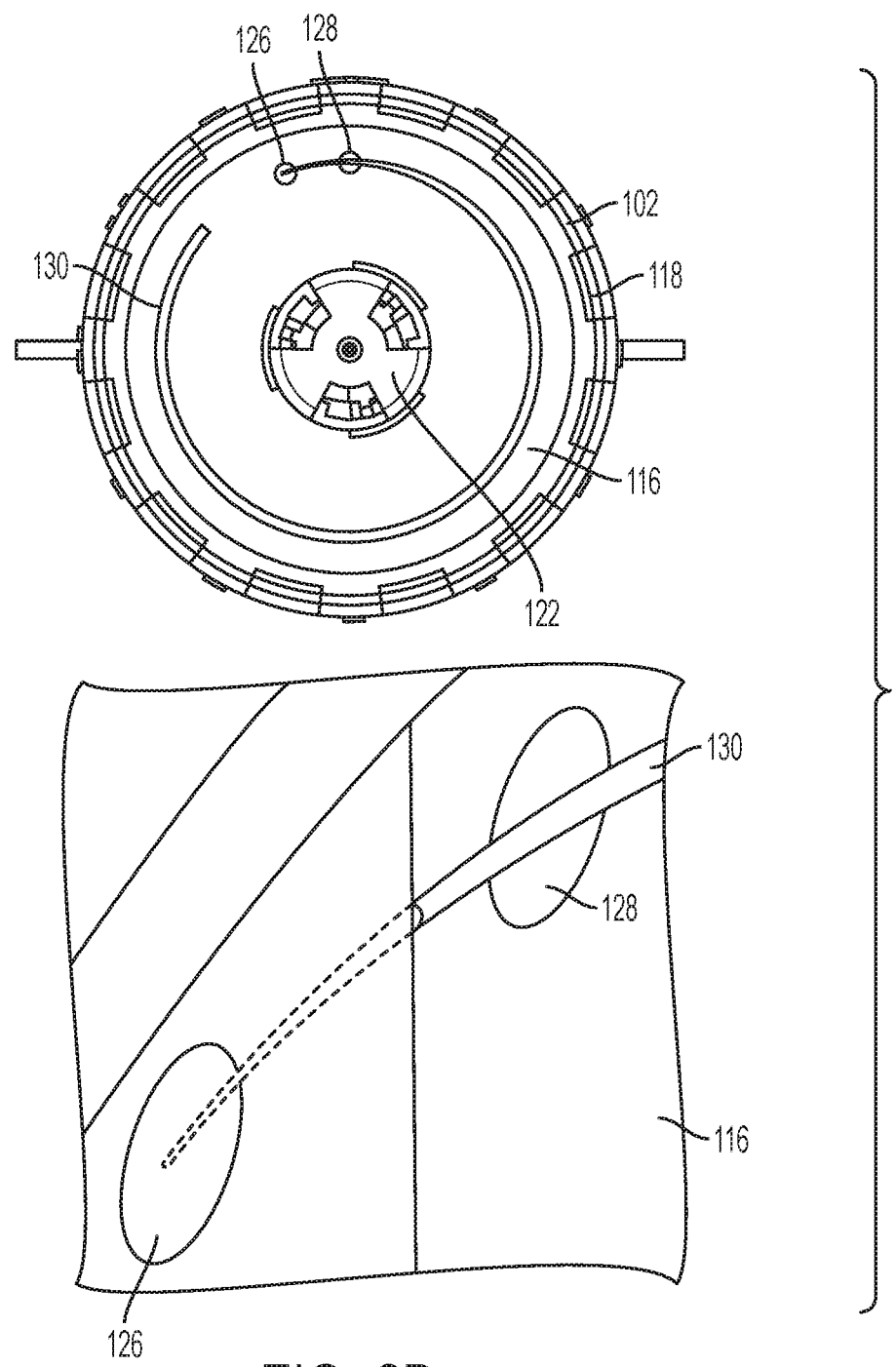
FIG. 2B illustrates an end view and a detail isometric view of the exemplary fluid flow regulator in a second operational state.

FIG. 2B shows the fluid flow regulator 106 in a second selectable position or a "1" position of the flow channel selector plate 118. In the "1" position, a small cross-sectional portion of the fluid flow channel 130 is coupled between the first and second openings 126 and 128 of the compliance plate 116, enabling some (e.g., limited) flow of liquid drug from the drug container 102. The detailed view of the compliance plate 116 shows a portion of the fluid flow channel in dash to reveal the changing cross-sectional dimensions of the fluid flow channel coupled across the first and second opening s 126 and 128 as the selectable positions of the fluid flow selector plate 118 are changed.

Figure 3A:
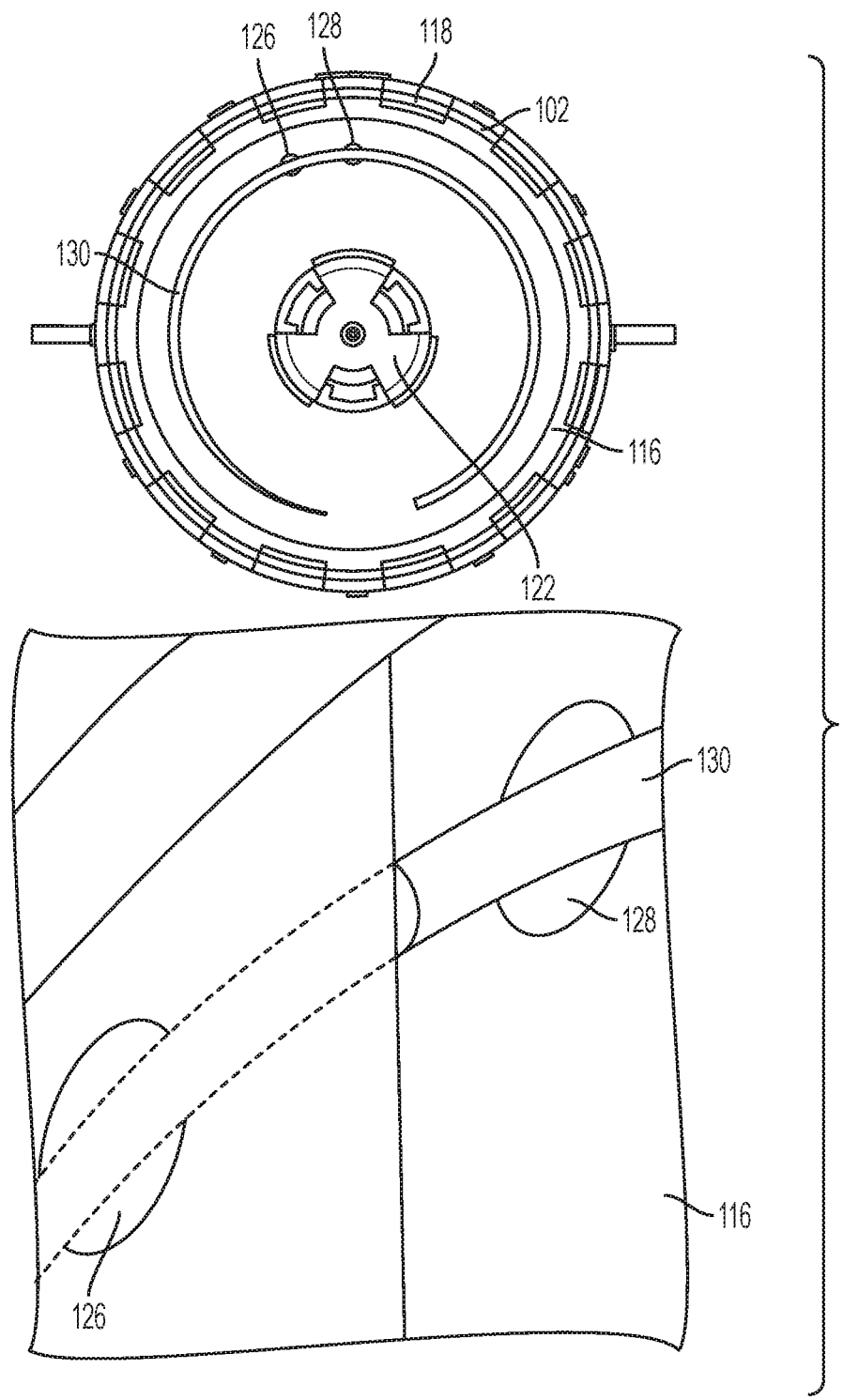
FIG. 3A illustrates an end view and a detail isometric view of the exemplary fluid flow regulator in a third operational state.

FIG. 3A shows the fluid flow regulator 106 in another selectable position or the "6" position of the flow channel selector plate 118. In the "6" position, a larger cross-sectional portion of the fluid flow channel 130 is coupled between the first and second openings 126 and 128 of the compliance plate 116, enabling greater flow of liquid drug from the liquid drug container 102 as compared to position "1" depicted in FIG. 2B.

Figure 3B:
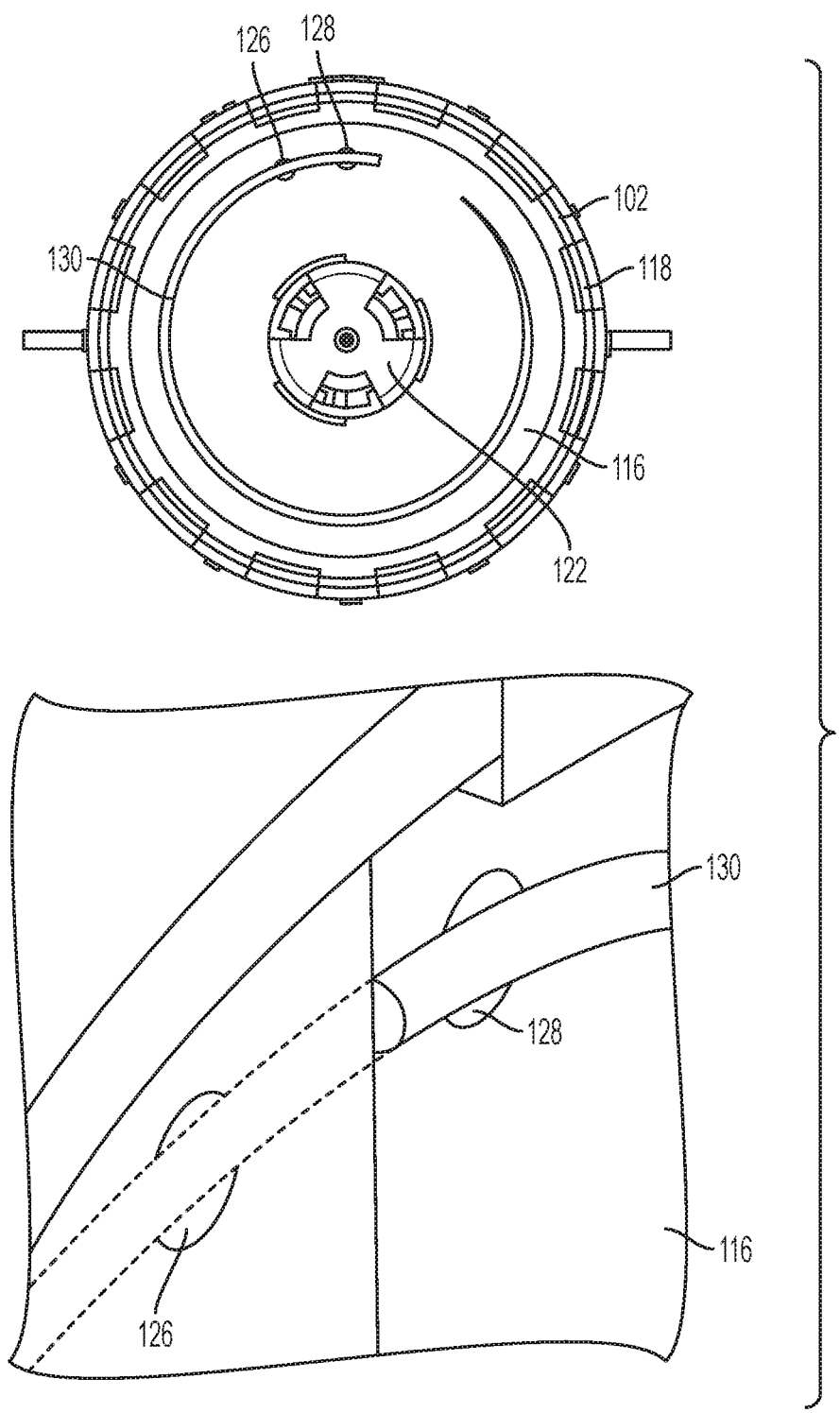
FIG. 3B illustrates an end view and a detail isometric view of the exemplary fluid flow regulator in a fourth operational state.

FIG. 3B shows the fluid flow regulator 106 in a maximum or "10" position of the flow channel selector plate 118. In the "10" position, the largest cross-sectional portion of the fluid flow channel 130 is coupled between the first and second openings 126 and 128 of the compliance plate 116, enabling greater flow of liquid drug from the liquid drug container 1 as compared to position "6" as depicted in FIG. 3A.

As can be seen, the distance between the first and second openings 126 and 128 of the compliance plate 116 stays constant, regardless of the position of the flow channel selector plate 118 (e.g., since the compliance plate 116 remains stationary). However, the position of the flow channel selector plate 118 can determine the size of (e.g., the cross-sectional portion of) the fluid flow channel 130 positioned between the first and second openings 126 and 128. Flow between the first and second openings 126 and 128 can be increased as the size of the cross-sectional portion of the fluid flow channel 130 is increased (and correspondingly decreased as the size of the cross-sectional portion of the fluid flow channel 130 is decreased). Thus, flow through the fluid flow regulator 106 is adjusted by changing the characteristics of the fluid flow channel 130 that is disposed across the first and second openings 126 and 128. The adjusted flow can then be coupled to the patient or user through, for example, the hard needle 124.

In various embodiments, the fluid flow channel 130 is a circular tapered channel. For example, the fluid flow channel 130 tapers from an initial height to a final height, with either the initial or final height being a maximum height or minimum height. In other embodiments, the profile of the fluid flow channel 130 can take on any shape or profile or tapering provided a final height is reached from a starting height. Accordingly, as the flow channel selector plate 118 is rotated, a different portion of the circular tapered channel forming the fluid flow channel 130 is exposed to the first and second openings 126 and 128. Lower settings of the flow channel selector plate 118 correspond to the first and second openings 126 and 128 being exposed to smaller cross-sectional portions of the circular tapered channel. Higher settings of the flow channel selector plate 118 correspond to the first and second openings 126 and 128 being exposed to larger cross-sectional portions of the circular tapered channel. In some embodiments the fluid flow channel 130 comprises a circular tapered channel molded into the flow channel selector plate 118. Overall, the fluid flow channel 130 can be coupled to the flow channel selector plate 118 in any manner.

Figure 4:
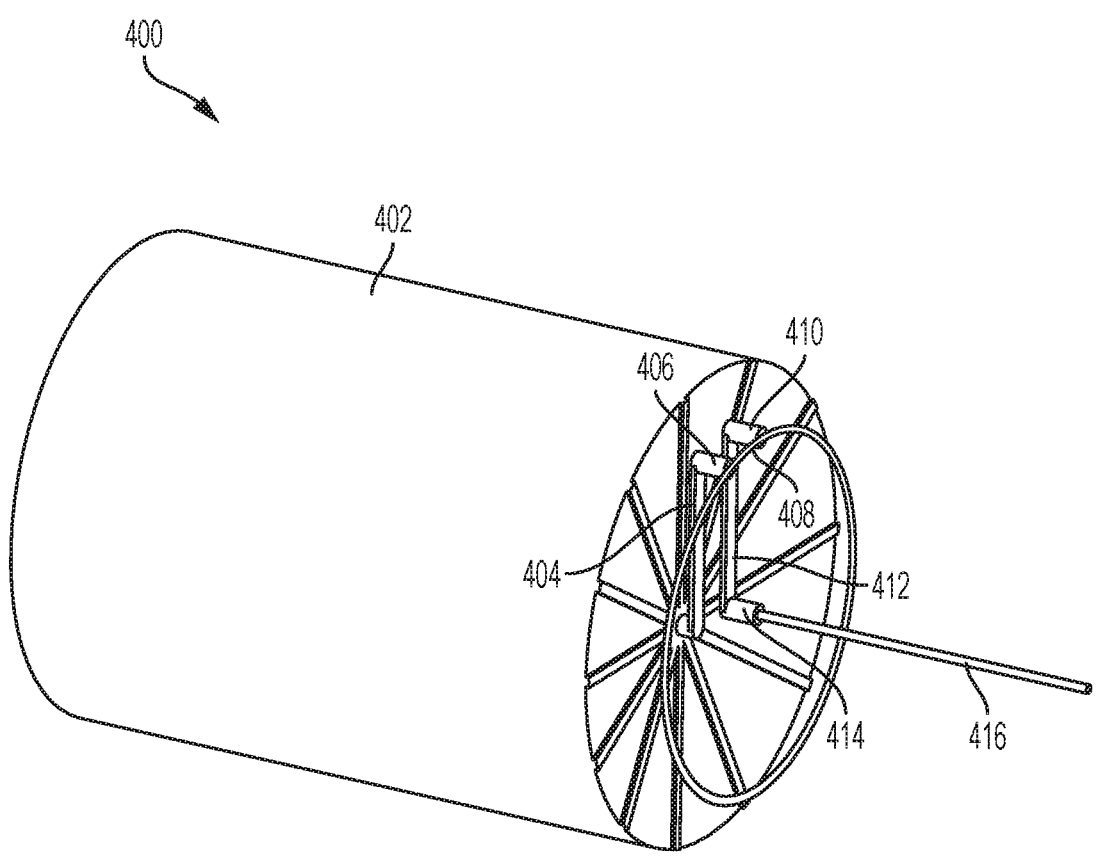
FIG. 4 illustrates a representational fluid flow diagram of the first exemplary drug delivery system.

FIG. 4 illustrates a fluid flow diagram 400 illustrating the flow path of a liquid drug from the liquid drug container 102 to the hard needle 124. Flow portion 402 represents the fluid as stored in the liquid drug container 102. Flow exits the liquid drug container 102 through an opening in the second end 110 of the container 102 and is directed, via flow path 404 through an inlet manifold 112 (see FIG. 1) formed in the second end 110 of the container 102. Flow path 406 represents the flow of liquid through the first opening 126 in the compliance plate 116. Flow path 408 represents the flow of liquid from the first opening 126 though the fluid flow channel 130 of the flow channel selector plate 118. Flow path 410 represents the flow of liquid from the fluid flow channel 130 back through the second opening 128 in the compliance plate 116. Flow path 412 represents the flow of liquid from the second opening 128 through an outlet manifold 114 (see FIG. 1) formed in the second end 110 of the liquid drug container 102. Flow path 414 represents the flow of liquid from the outlet manifold 114 to a third opening 132 in the compliance plate 116. From there, flow path 416 represents the flow of liquid from the third opening 132 out through the hard needle 124 (e.g., through a central opening of the flow channel selector plate).

Figure 5A:
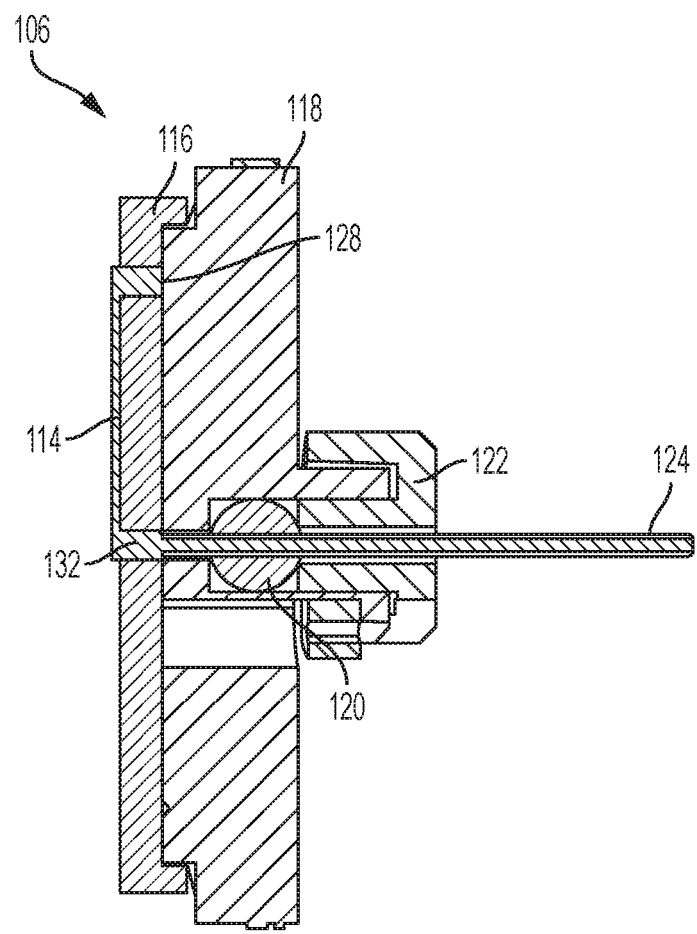
FIG. 5A illustrates a cross-sectional side view of the exemplary fluid flow regulator.
Figure 5B:
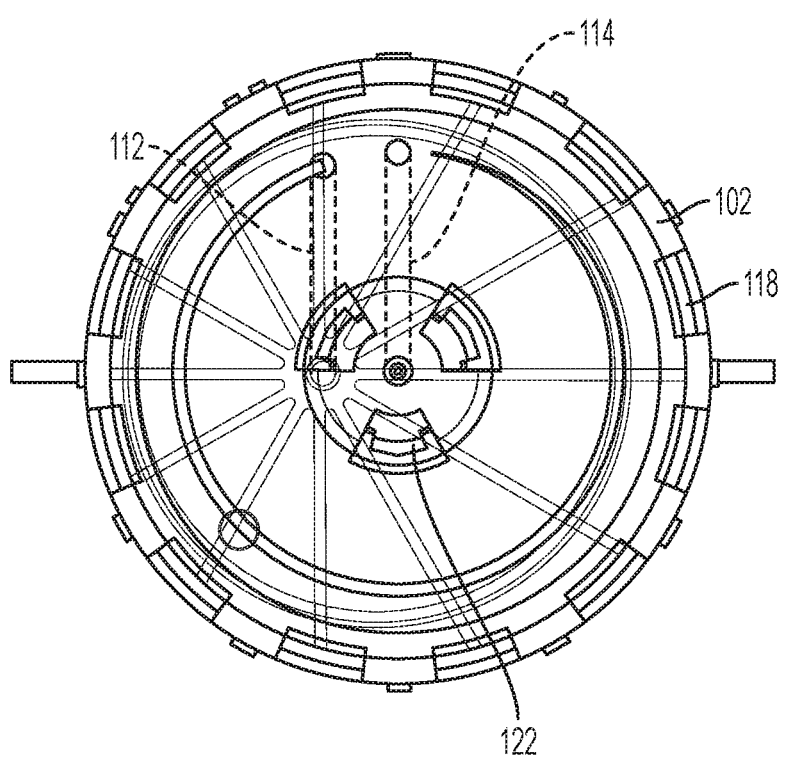
FIG. 5B illustrates an end view of the exemplary fluid flow regulator.

Aspects of the fluid flow passages through the liquid drug container 102 (e.g., the inlet and outlet manifolds 112 and 114), and the compliance plate 116 (e.g., the second and third openings 128 and 132), as well as their connections to the needle 124 are illustrated in FIGS. 5A and 5B. Specifically, FIG. 5A shows a cross-sectional side view of the fluid flow regulator 106. As shown in FIG. 5A, the second opening 128 is coupled to the outlet manifold 114, the outlet manifold 114 is coupled to the third opening 132, and the third opening 132 is coupled to the hard needle 124, thereby completing a fluid path based on a selected regulated flow from the container 102 to the needle 102. As further shown in FIG. 5A, the needle ball 120 and the needle ball retainer 122 can support the needle 124.

FIG. 5B shows a rear view of the fluid flow regulator 106 (e.g., as viewed looking toward the needle ball retainer 122 from the needle 124). As shown, the manifolds 112 and 114 are shown providing part of the fluid path from the container 102 to the hard needle 124.

Figure 6:
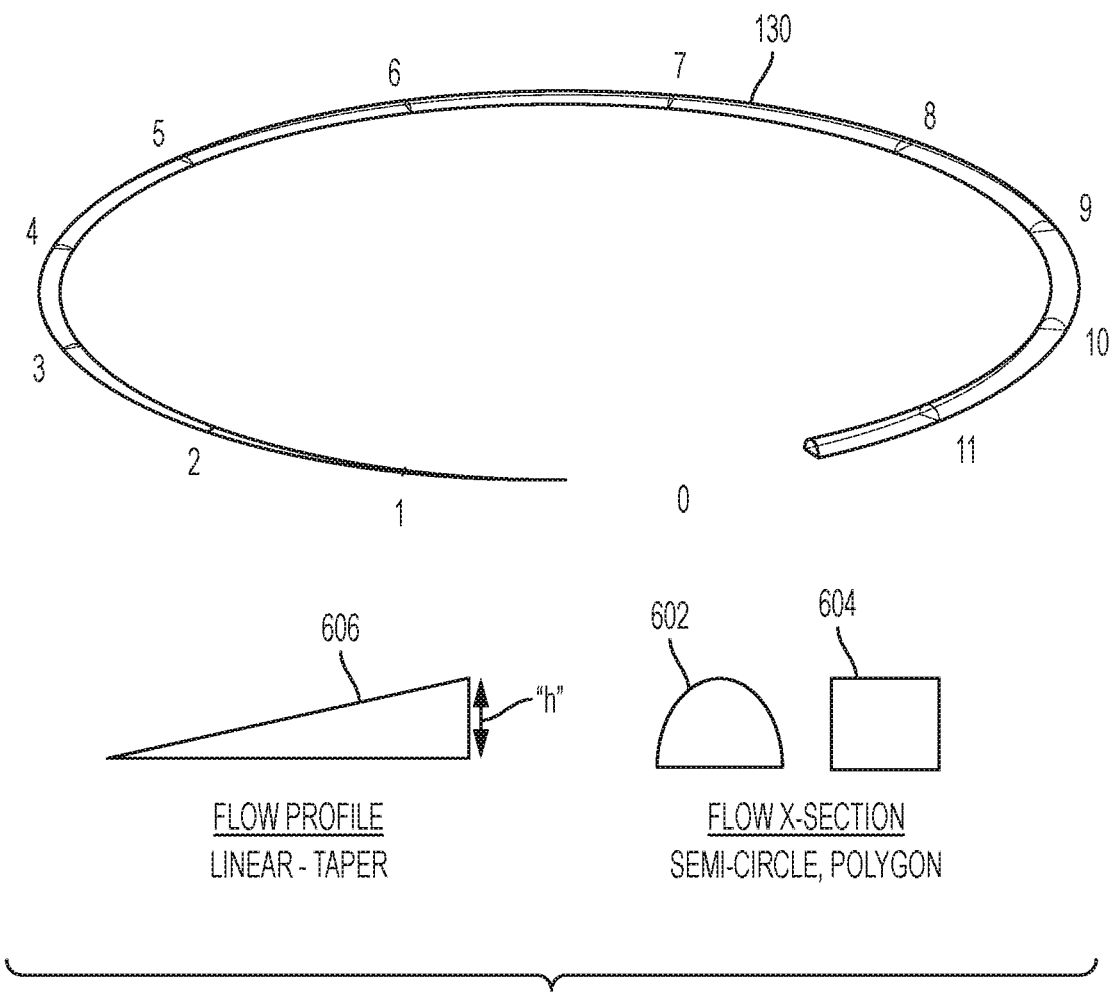
FIG. 6 illustrates an exemplary flow profile and exemplary flow cross-sections provided by an exemplary fluid flow channel of the exemplary fluid flow regulator.

FIG. 6 shows an isometric representation of the fluid flow channel 130 as a circular channel with a tapering cross-section. FIG. 6 also shows an example flow profile 606 of the fluid flow channel 130. The example flow profile 606 of the fluid flow channel 130 can have a constantly tapering height "h" that has a largest or maximum height at a setting "11" and that has a smallest or minimum height at a setting "0". As mentioned, lower settings of the flow channel selector plate 118 correspond to the first and second openings 126 and 128 of the compliance plate 116 being exposed to smaller cross-sectional portions of the circular tapered channel of the fluid flow channel 130, while higher settings of the flow channel selector plate 118 correspond to the first and second openings 126 and 128 being exposed to larger cross-sectional portions of the circular tapered channel of the fluid flow channel 130. As shown in FIG. 6, the flow profile 606 has a height "h" that smoothly and linearly moves from a minimum height to a maximum height over the length of the fluid flow channel 130. In various embodiments, the change in the height "h" can be non-linear.

FIG. 6 further illustrates example cross-sectional shapes of the fluid flow channel 130. As an example, a first cross-sectional shape 602 can be a semi-circle or half-circle. A second cross-sectional shape 604 can be a polygon (e.g., a square). It will be appreciated, however, that any of a variety of cross-sectional shapes (e.g., polygonal or other geometric and non-geometric shapes) can be used, as can cross-sectional shapes that change along the length of the fluid flow channel 130 (e.g., such that the fluid flow channel 130 includes two or more cross-sectional shapes or varies in any manner along the length of the fluid flow channel 130).

In some embodiments, the tapered channel(s) of the fluid flow channel 130 may have gradual/helical tapers or distinct steps where high resolution low flow performance can be achieved within some set amount of degrees or radians, while the more "wide open" end can provide a bolus.

Figure 7:
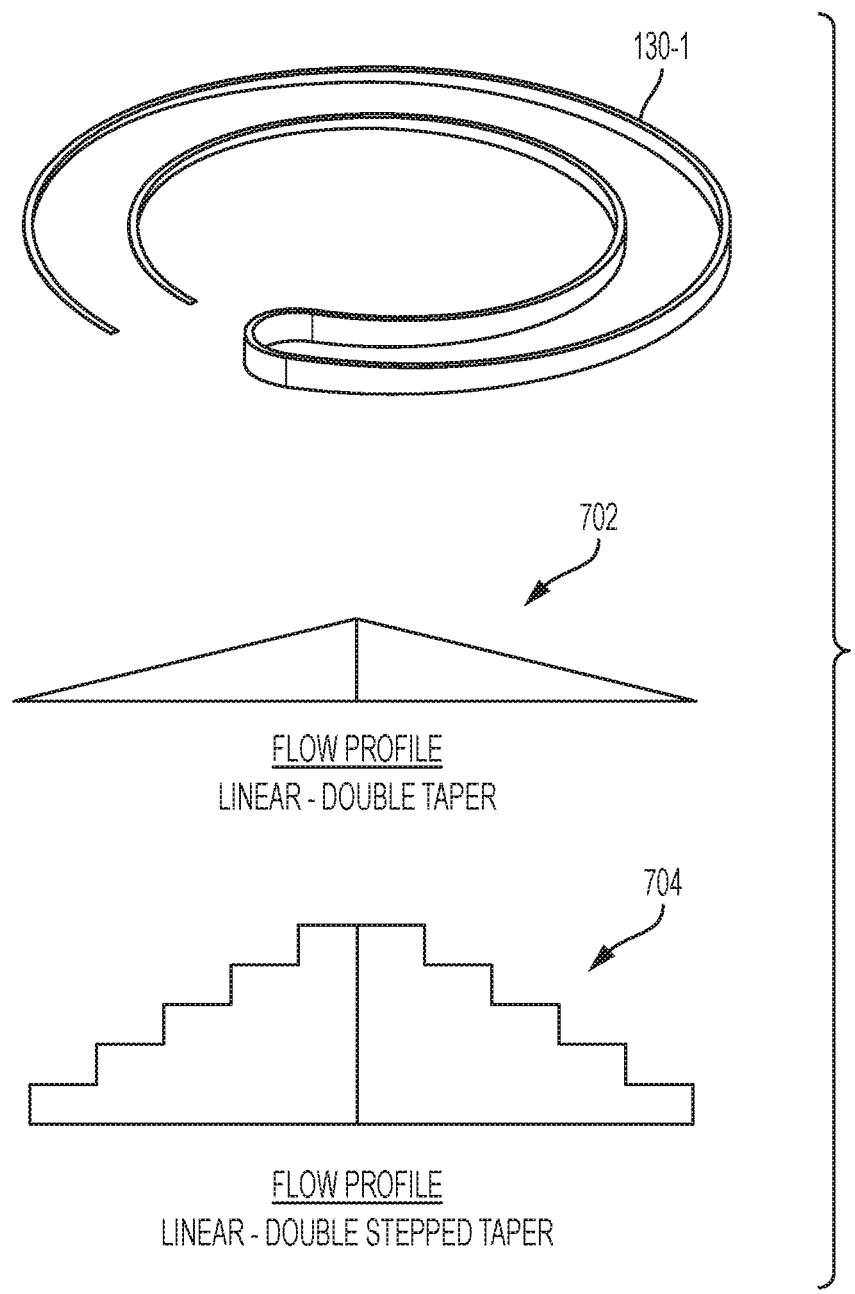
FIG. 7 illustrates exemplary flow profiles provided by an alternative exemplary fluid flow channel of the exemplary fluid flow regulator.

FIG. 7 illustrates an alternative embodiment 130-1 of the fluid flow channel 130 comprising a double channel that snakes around the face of the flow channel selector plate 116. In various embodiments, a double channel can include an inner circular portion and an outer circular portion, each coupled to a different opening 126 and 128 (see FIGS. 8A-8E).

In the illustrated embodiment shown in FIG. 7, the fluid flow channel 130 can include a linear double-tapered configuration such that fluid in the fluid flow channel 130 is forced through a loop that also tapers. As shown, a first open end of the double channel can have a minimum height, a second open end of the double channel can also have the minimum height, and between the open ends the height can increase to a maximum height and then back to the minimum height.

FIG. 7 also shows exemplary flow profiles. For example, a flow profile 702 can correspond to the embodiment of the fluid flow channel 130-1 shown in FIG. 7 having a linear double-tapered configuration (e.g., tapers from a maximum height from a halfway position of the channel down to a minimum height at the open ends of the channel). A flow profile 704 is also shown in which the taper or change in the fluid flow channel 130-1 is stepped rather than linear. As an example, the steps can be discontinuous changes in the height of the channel. The steps can be the same increases or changes or height or can vary and can be spaced evenly along the length of the channel or can vary. It will be appreciated that the fluid flow channel 130-1 can be provided with any of a variety of profiles to achieve a desired flow response along any portion of a length of the fluid flow channel 130 including one or more different flow profiles. Further, the double channeled fluid flow channel 130-1 can have any cross-sectional shape along any portion of the fluid flow channel 130-1. In general, any fluid channel disclosed herein can have any flow profile (e.g., linearly or non-linearly changing along the length of the channel) and any cross-sectional shape.

FIGS. 8A through 8E illustrate various selected flow paths through the "loop style" or double channel fluid flow channel 130-1 depicted in FIG. 7. Specifically, FIGS. 8A through 8E show the first and second openings 126 and 128 coupled to different portions of the fluid flow channel 130-1. In various embodiments, for a "loop style" fluid flow channel 130, the first and second openings 126 and 128 can be positioned along a same radial axis extending from a center of the compliance plate 116—for example, such that the first opening 126 is positioned further from the center of the compliance plate than the second opening 128.

Figure 8A:
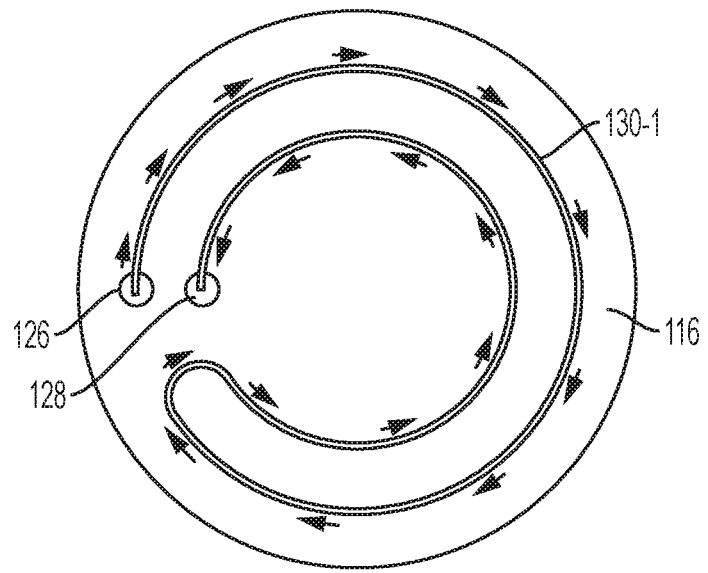
FIG. 8A illustrates a first flow scheme for exemplary fluid flow regulator.
Figure 8B:
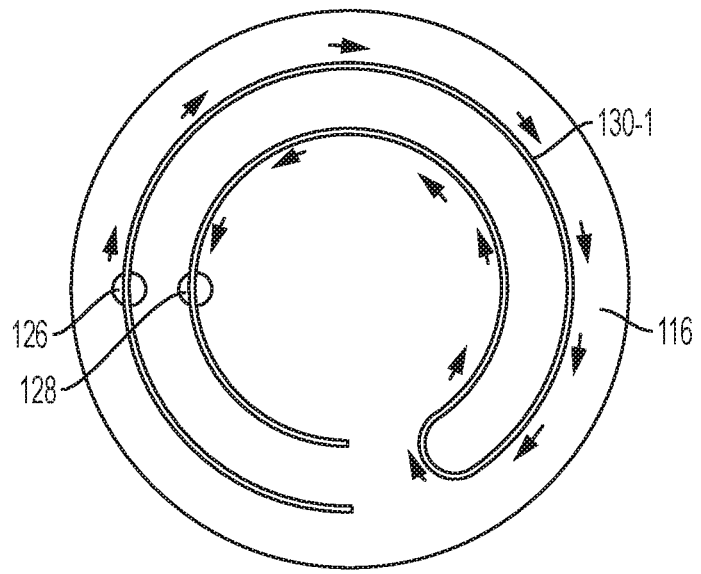
FIG. 8B illustrates a second flow scheme for exemplary fluid flow regulator.
Figure 8C:
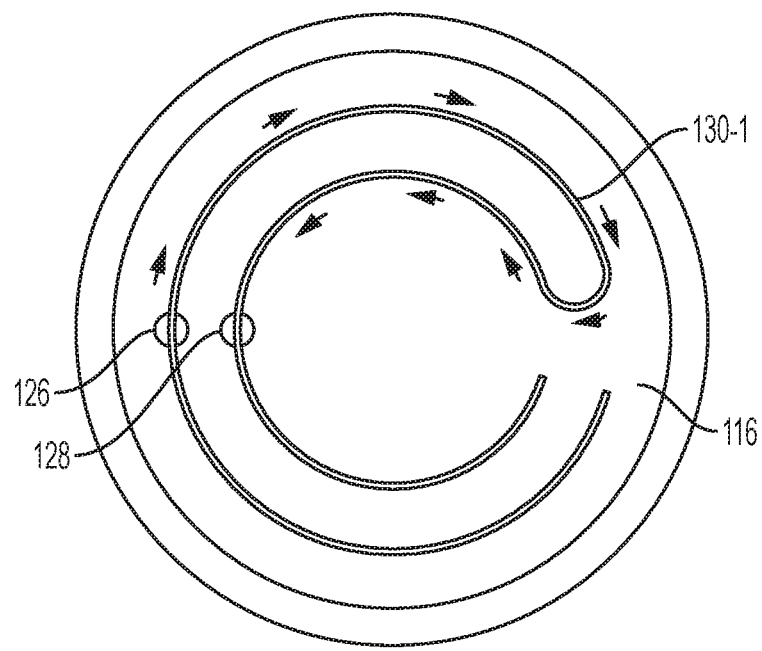
FIG. 8C illustrates a third flow scheme for exemplary fluid flow regulator.
Figure 8D:
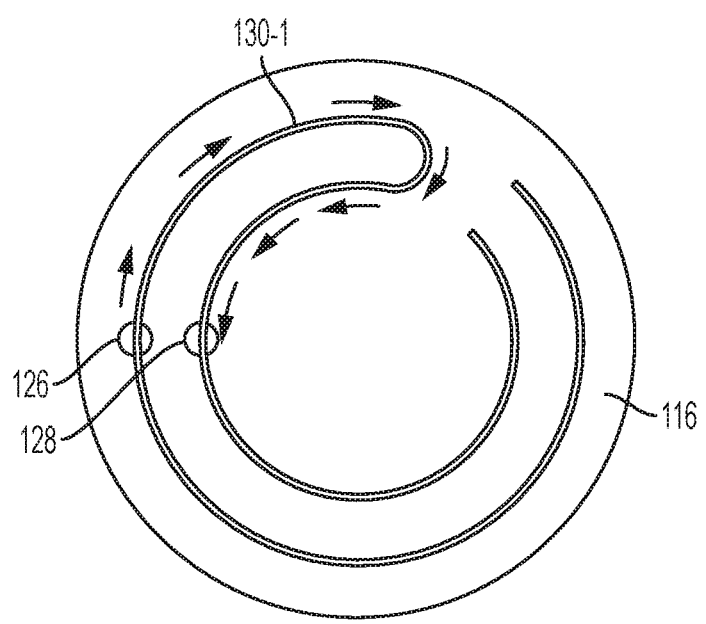
FIG. 8D illustrates a fourth flow scheme for exemplary fluid flow regulator.
Figure 8E:
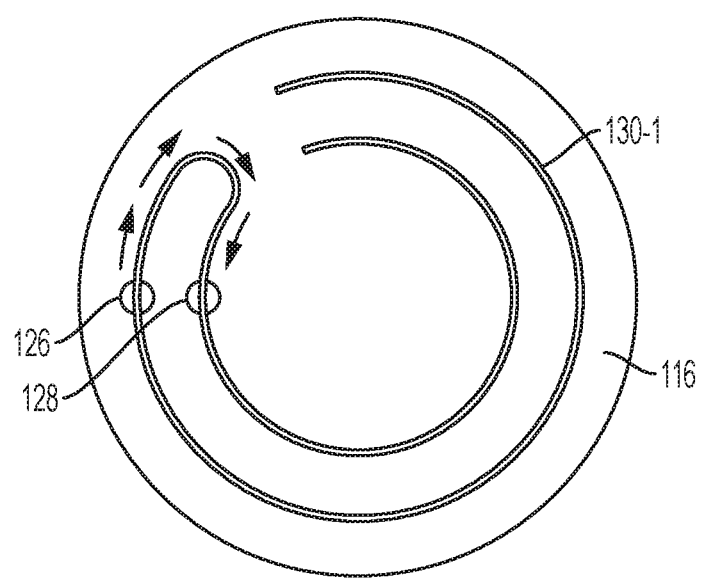
FIG. 8E illustrates a fifth flow scheme for exemplary fluid flow regulator.

FIG. 8A shows the first and second openings 126 and 128 coupled to a first portion of the fluid flow channel 130-1, FIG. 8B shows the first and second openings 126 and 128 coupled to a second portion of the fluid flow channel 130-1, FIG. 8C shows the first and second openings 126 and 128 coupled to a third portion of the fluid flow channel 130-1, FIG. 8D shows the first and second openings 126 and 128 coupled to a fourth portion of the fluid flow channel 130-1, and FIG. 8E shows the first and second openings 126 and 128 coupled to a fifth portion of the fluid flow channel 130-1. As shown, the first opening 126 can be coupled to one of the two channels of the fluid flow channel 130-1 (e.g., one side of the fluid flow channel 130-1) and the second opening 128 can be coupled to the other of the two channels of the fluid flow channel 130-1 (e.g., the other side of the fluid flow channel 130-1).

As can be seen, when the flow channel selector plate 130 is rotated to position the fluid flow channel 130-1 in the orientation of FIG. 8A, liquid drug is forced through the entire length of the flow loop of the fluid flow channel 130-1 between the first and second openings 126 and 128 in the compliance plate 116 (e.g., across all portions of both channels as indicated by the flow arrows). This may be associated with position "1" of the flow channel selector plate 118 as it represents the highest amount of fluid resistance available with the illustrated fluid flow channel 130. The illustrated arrows can show a flow of a liquid through the channel 130-1.

When the flow channel selector plate 130 is rotated to position the fluid flow channel 130-1 in the orientation of FIG. 8B, liquid drug is force through a slightly reduced length of the fluid flow channel 130-1 as compared to the FIG. 8A orientation. FIGS. 8C-8E show incrementally reduced lengths of the fluid flow channel 130-1 through which liquid drug will flow, which may correspond with respectively reduced flow resistance through the fluid flow channel 130-1 (since less distance is traversed by the liquid drug as increasingly reduced portions of each channel are traversed). FIG. 8E may correspond with the highest level of the flow channel selector plate 118—for example, representing maximum flow and lowest flow resistance.

Figure 9:
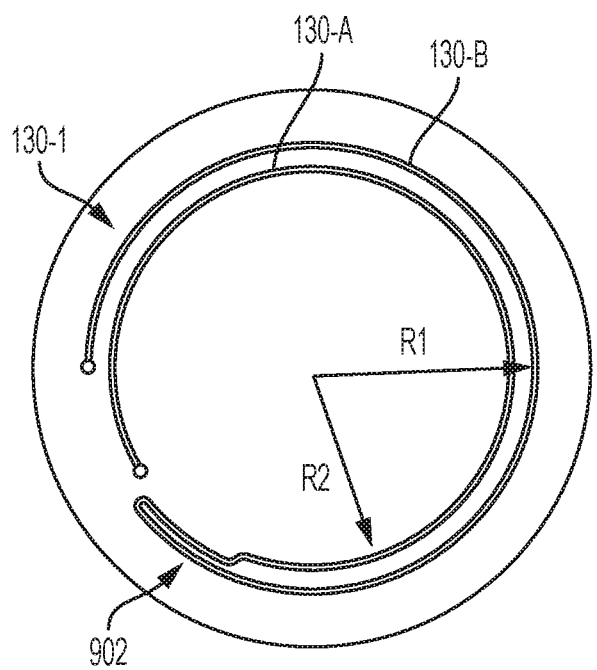
FIG. 9 illustrates an arrangement for equalizing the flow legs of the fluid flow regulating device depicted in FIGS. 8A-8E.

FIG. 9 illustrates an arrangement for maintaining the lengths "equal" between the inner and the outer loops (or channels) 130-A and 130-B of the fluid flow channel 130-1 in order to obtain a linear output, for example when the fluid flow channel 130 is implemented in a "loop style" (e.g., as fluid flow channel 130-1 as shown in FIG. 7). In this embodiment, an unconstrained section 902 is positioned where the inner and outer loops 130-A and 130-B meet. As will be appreciated, since the outer loop 130-B has a radius R1 that is greater than the radius R2 of the inner loop 130-A, the loops 130-A and 130-B will not be the same length. In some embodiments the positions of the inlet (at the first opening 126 in the compliance plate 116) and the outlet (at the second opening 128 in the compliance plate 116) could be varied, or a deep channel (unconstrained section 902) could be positioned at the end of the longer outer loop 130-B to "normalize" the lengths of the inner and outer loops 130-A and 130-B.

Figure 10A:
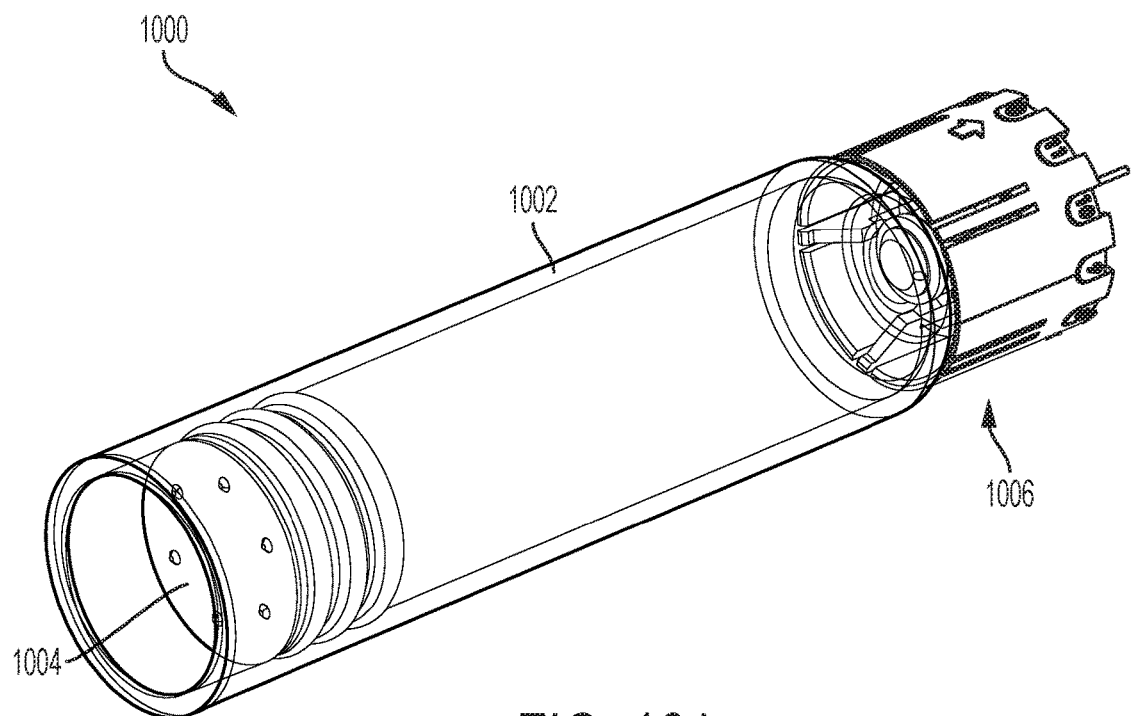
FIG. 10A illustrates an isometric view of a second exemplary drug delivery system.
Figure 10B:
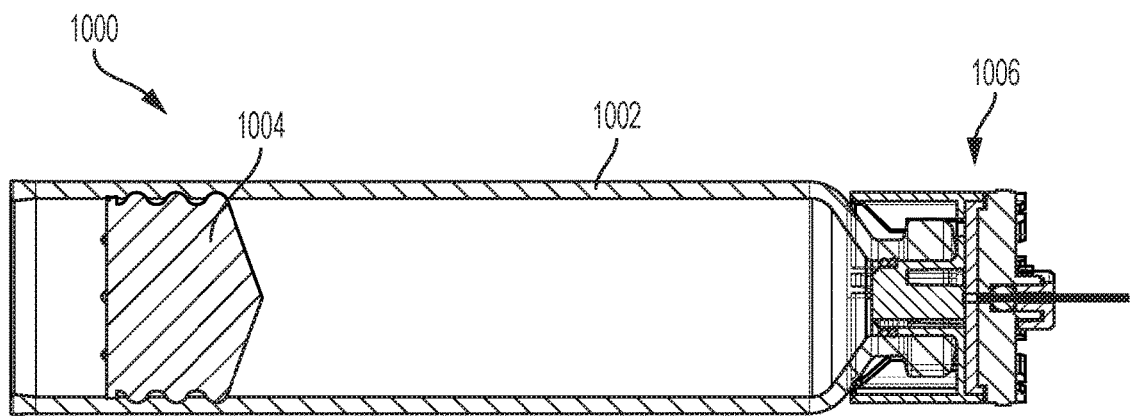
FIG. 10B illustrates a cross-sectional side view of the second exemplary drug delivery system
Figure 10C:
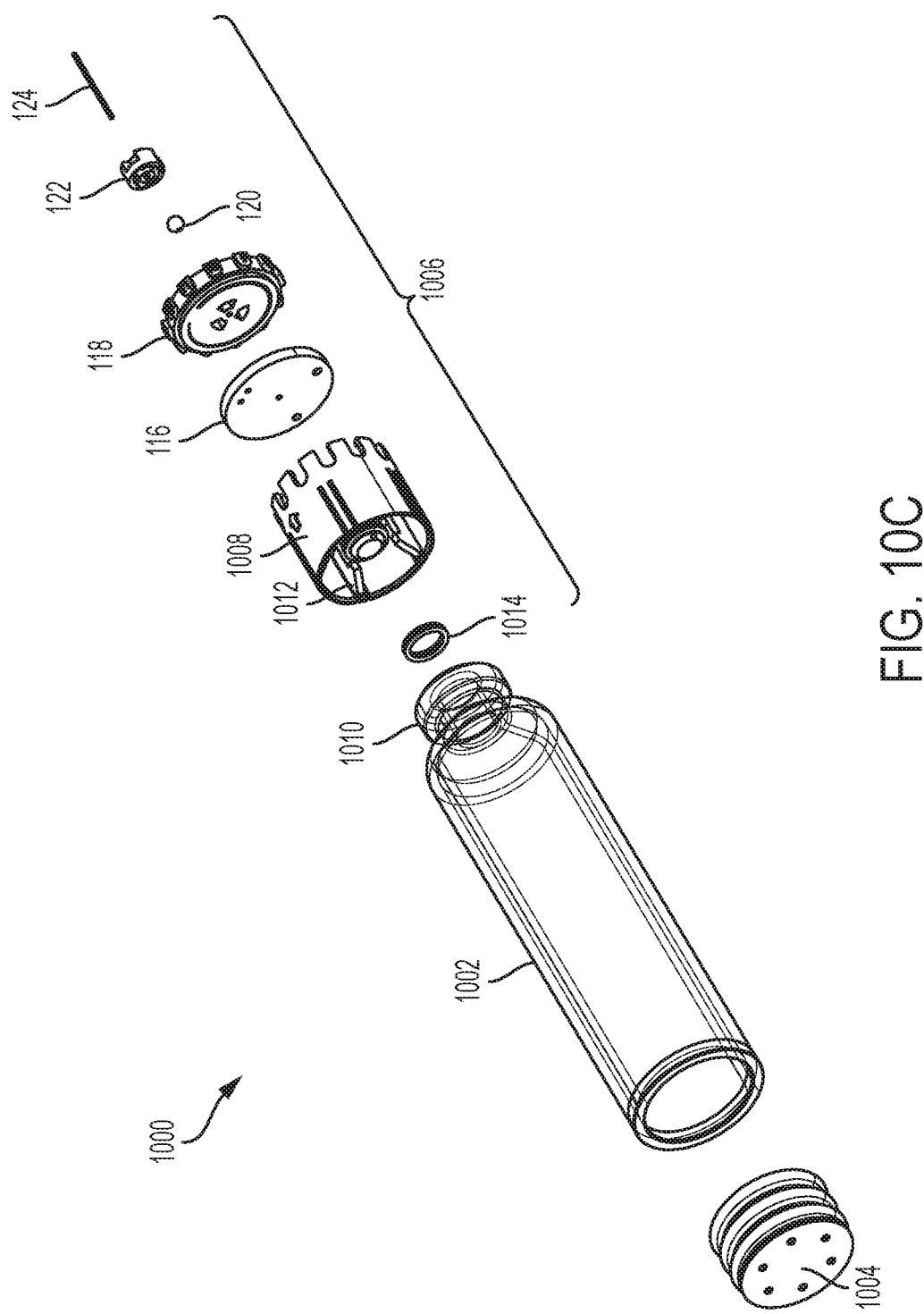
FIG. 10C illustrates an exploded view of the second exemplary drug delivery system.

FIGS. 10A through 10C illustrate a drug container system 1000 (or liquid drug container system). FIG. 10A shows a first view of the drug container system 1000 in an assembled state. FIG. 10B shows a cross-sectional side view of the drug container. FIG. 10C shows an exploded view of the drug container system 1000 to illustrate the arrangement of the constituent components of the drug container system 1000. The drug container system 1000 can store or hold any liquid drug or any other fluid or therapeutic agent.

As shown in FIGS. 10A through 10C, the drug container system 1000 can include a drug container 1002 (or liquid drug container), a plunger 1004, and a fluid flow regulator 1006. The drug container 102 may be an International Organization for Standardization (ISO) cartridge (e.g., made of glass). Accordingly, the drug container system 1000 illustrates a fluid flow regulator 1006 that can be coupled to a standard ISO glass cartridge 1002.

The features present in the second end 110 of the liquid drug container 102 of FIGS. 1A and 1B (e.g., the inlet and outlet manifolds 112 and 114) can be incorporated into a cartridge adapter 1008. The cartridge adapter 1008 may have features that enable it to snap onto a mouth portion or opening 1010 (e.g., a neck and crown) of the liquid drug container 1002. In various embodiment these features can include flexible snaps 1012 that can flex outward when pressed against the mouth portion 1010 and then expand behind the mouth portion 1010 to lock the cartridge adapter 1008 in place.

An annular seal 1014 such as an O-ring may seal the cartridge adapter 1008 to the liquid drug container 1002. The compliance plate 116 and the flow channel selector plate 118 of the drug container system 1000 may have the same features and functionality as described in relation to the drug container system 100. The needle ball 120, needle ball retainer 122, and the hard needle 124 may also be the same as described in relation to the drug container system 100.

Figure 11:
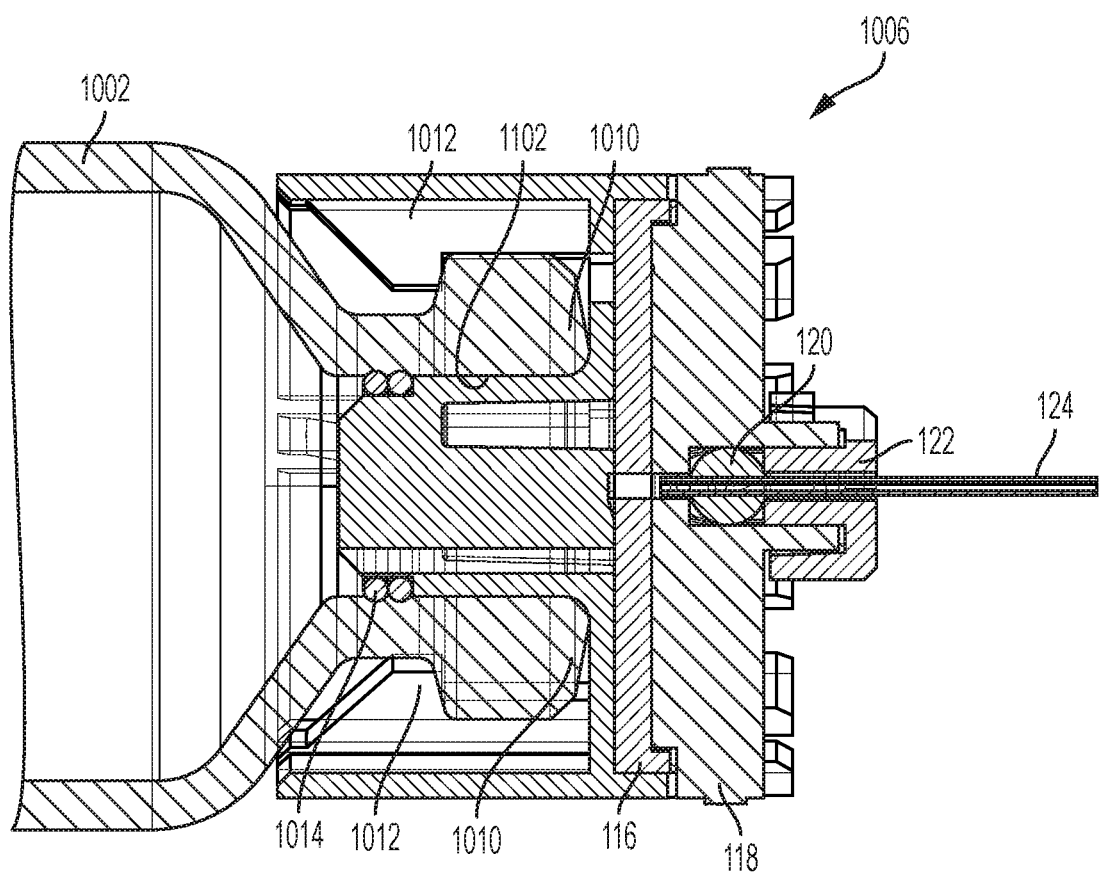
FIG. 11 illustrates a detailed view of an exemplary fluid flow regulator depicted in FIGS. 10A-10C.

FIG. 11 shows and inter-engagement between the liquid drug container 1002 and the fluid flow regulator 1006 depicted in FIGS. 10A-10C. As can be seen, the annular seal 1014 may seal against an internal surface 1102 of the liquid drug container. The flexible snaps 1012 are shown in a locked position, sitting behind the mouth portion 1010 of the liquid drug container 1002. The compliance plate 116 can be coupled to the cartridge adapter 1008. The flow channel selector plate 118 can be pressed against the compliance plate 116 and can also be positioned or disposed within the cartridge adapter 1008.

Figure 12A:
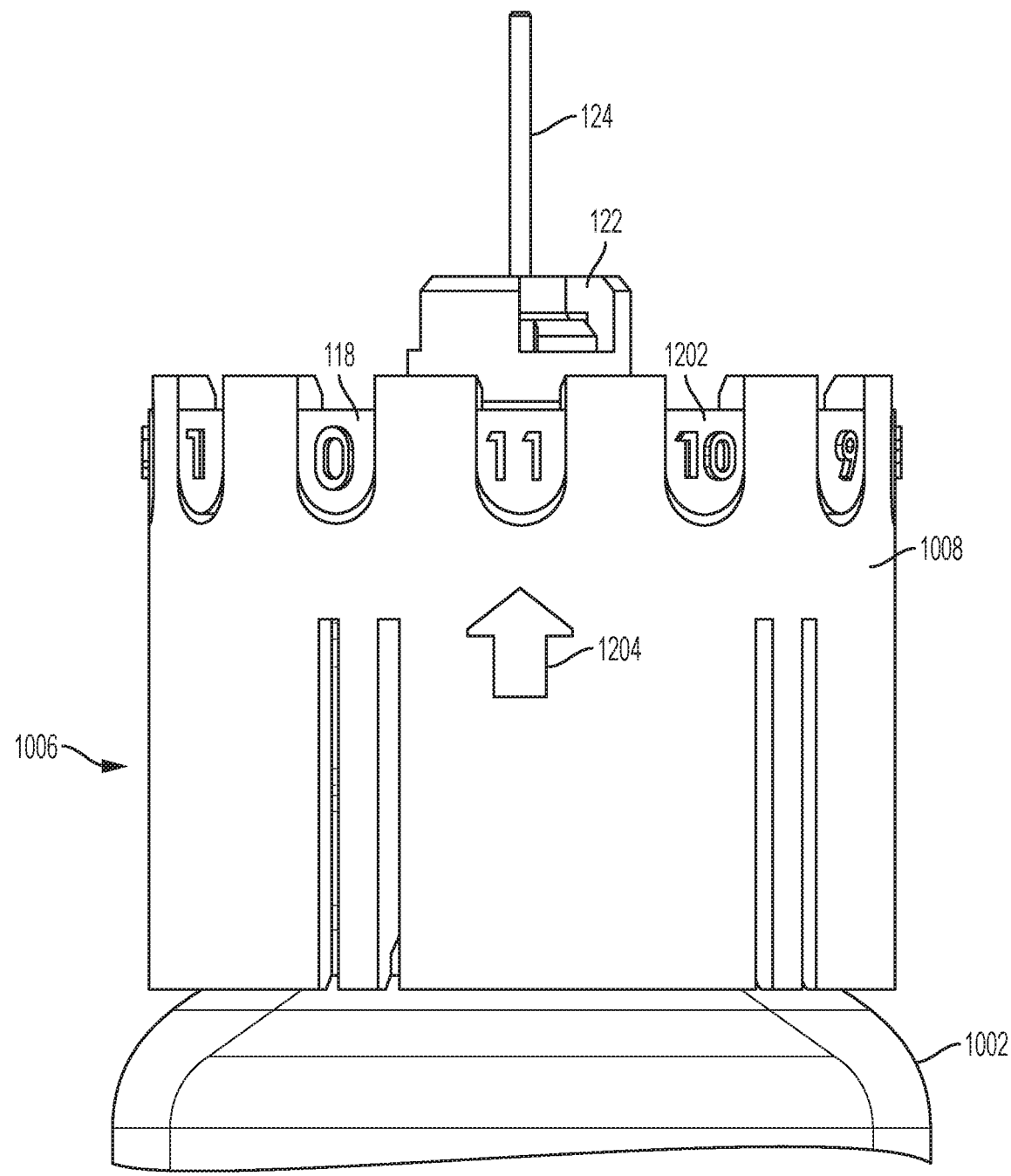
FIG. 12A illustrates a first exemplary embodiment for adjusting an exemplary fluid flow regulator.

FIG. 12A shows the fluid flow regulator 1006 incorporating a plurality of fixed, finite flow settings. As shown in FIG. 12A, the flow channel selector plate 118 can include a flow setting 1202 (e.g., set by rotating the flow channel selector plate 118) and the cartridge adapter 1008 can include a flow setting indicator 1204 to specify what flow setting 1202 is selected or set. As can be seen, a finite number of portions of the flow channel selector plate 118 (and therefore corresponding flow settings 1202) can be chosen or selected.

Figure 12B:
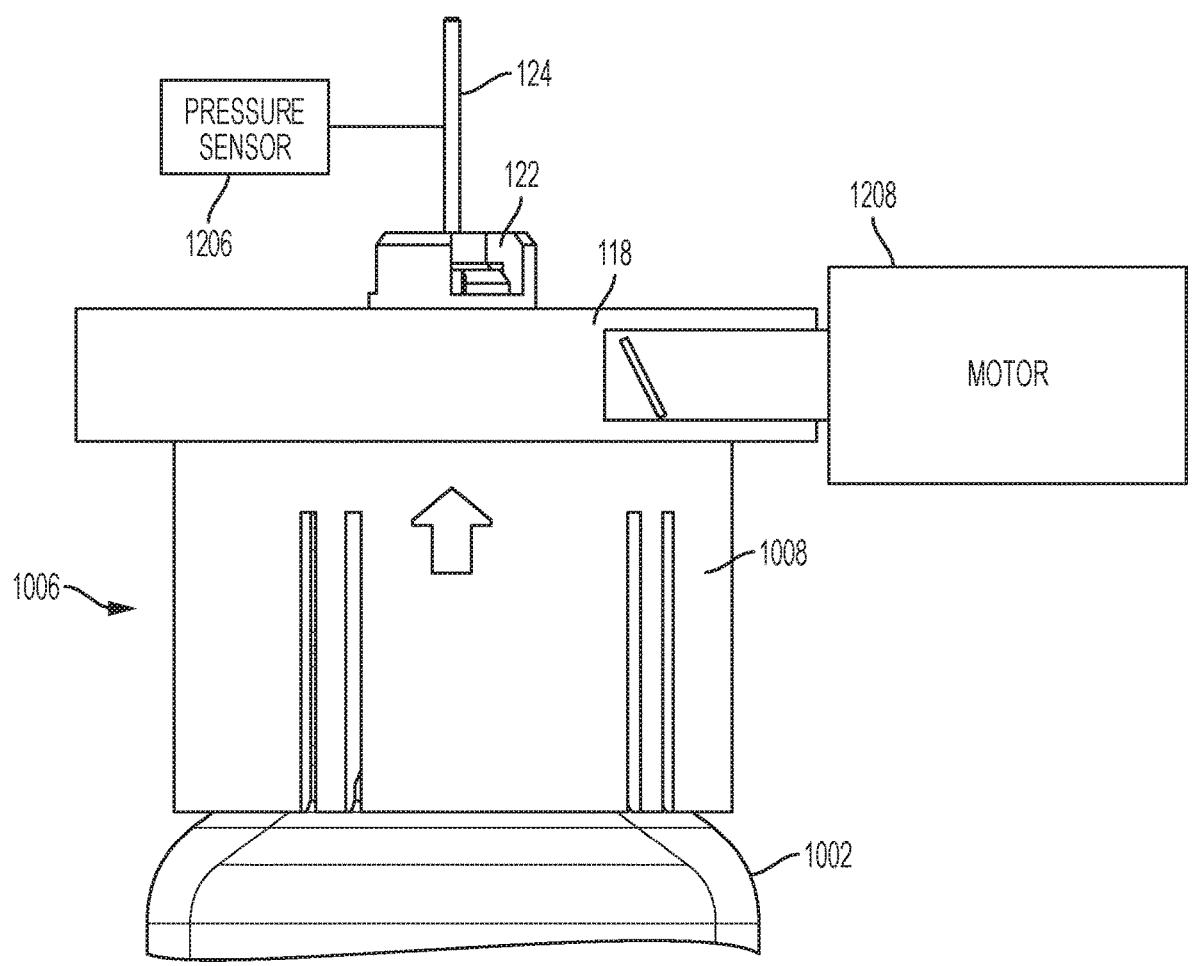
FIG. 12B illustrates a second exemplary embodiment for adjusting an exemplary fluid flow regulator.

Referring to FIG. 12B, for systems in which it may be important to maintain a constant basal rate, such as with insulin delivery, a closed loop approach can be applied in which a pressure sensor 1206 or plunger positioning sensor can sense flow rate or plunger position and can feed that information back to a flow regulation arrangement or component 1208, which may include a motor or other arrangement for adjusting the flow channel selector plate 118. In the exemplary embodiment of FIG. 12B, the flow channel selector plate 118 is infinitely adjustable, and is coupled to a motor 1208. As real-time sensed information is received from the pressure sensor 1206 (or plunger position sensor), the motor 1208 may be actuated to adjust the rotational position of the flow channel selector plate 118 to adjust the flow resistance through the fluid flow regulator 1006. For example, if the sensor 1206 indicates that flow is decreasing below a predetermined rate, the motor 1208 can be activated to adjust the position of the flow channel selector plate 118 to reduce flow resistance through the regulator to thereby re-establish flow to within the desired range. The exemplary arrangements depicted in FIGS. 12A and 12B can be applied to the drug container system 100 as well. As an example, the pressure sensor 1206 can be coupled to the needle 124, for example, to detect a flow or flow pressure of the liquid drug through the needle 124.

Referring now to FIGS. 13-16, to control fluid delivery rates with varying drive sources which may exhibit decay or rapid changes in drive pressure, a turbulent flow regime (e.g., Reynold's number greater than 4000) may be exploited to disrupt flow sufficiently that for a given increase in pressure, little impact on outlet flow rate will be experienced. FIGS. 13-16 illustrate various exemplary surface profiling arrangements that can be employed within the fluid flow channel 130 within any of the devices or systems described herein.

In various embodiments one or more of these surface profiling arrangements can be employed along the entire length of the fluid flow channel 130 or a portion thereof or according to any pattern (e.g., applied to distinct non-overlapping regions of the fluid flow channel 130). In various embodiments the surface profiling arrangements can be applied over a limited length of the fluid flow channel 130 to generate turbulent flow over a limited length followed by an area that converts flow back to the laminar regime. The surface profiling arrangements may be molded or textured interior features of the fluid flow channel 130 (e.g., any of the exemplary fluid flow channels described herein).

Figure 13:
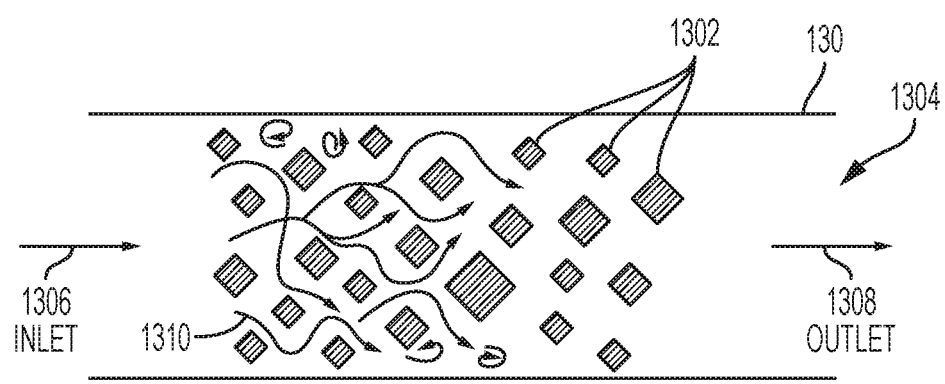
FIG. 13 shows a first exemplary surface profiling arrangement.

FIG. 13 shows a first exemplary surface profiling arrangement. Specifically, FIG. 13 shows a plurality of diamond-shaped protrusions 1302 positioned on an interior surface 1304 of the fluid flow channel 130. The protrusions 1306 can be oriented so that the points of the diamond protrusions 1302 are aligned with a general flow of fluid between an inlet 1306 and an outlet 1308 of the fluid flow channel 130. Flow indicators 1310 shows the general flow of a fluid through the fluid flow channel 130. The diamond-shaped protrusions 1302 may be of varying heights with respect to the height "h" of the fluid flow channel 130. Alternatively, the protrusions 1302 could have different orientations and/or could be of a consistent height.

Figure 14:
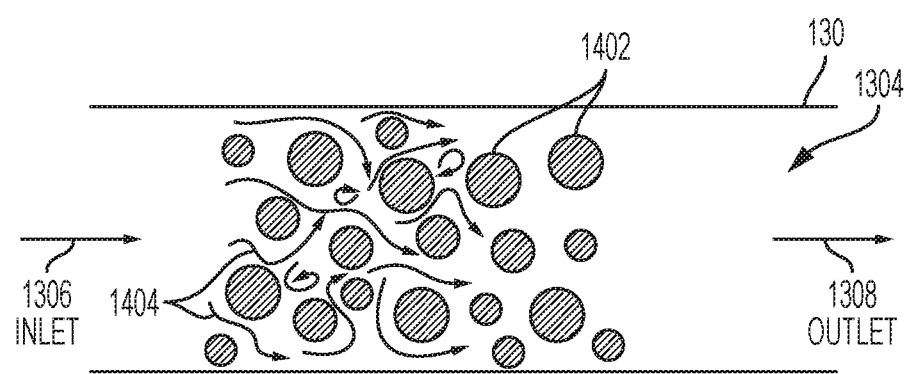
FIG. 14 shows a second exemplary surface profiling arrangement.

FIG. 14 shows a second exemplary surface profiling arrangement. Specifically, FIG. 14 shows a plurality of circular protrusions 1402 positioned on the interior surface 1304 of the fluid flow channel 130. Flow indicators 1404 show the general flow of a fluid through the fluid flow channel 130. As with the previous embodiment, the circular protrusions 1402 may be of varying heights with respect to the height "h" of the fluid flow channel 130. Alternatively, the protrusions 1402 could have different orientations and/or could be a consistent height. The circular protrusions 1302 may all have the same diameter or some may have different diameters.

Figure 15:
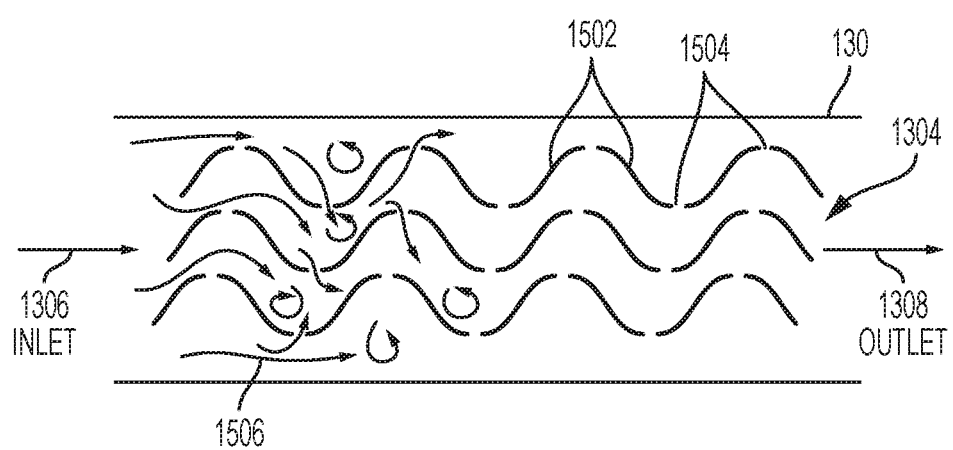
FIG. 15 shows a third exemplary surface profiling arrangement.

FIG. 15 shows a third exemplary surface profiling arrangement. Specifically, FIG. 15 shows a plurality of perforated undulating walls 1502 positioned on the interior surface 1304 of the fluid flow channel 130. The walls 1502 can include a plurality of openings or cross-channels 1504 that allow flow 1506 of the liquid to pass through the walls 1502 as the fluid travels from the inlet 1306 to the outlet 1308. The openings 1504 can be regularly spaced along the length of the walls 1502 or can be spaced at irregular intervals and can be of the same size or of different sizes. In the illustrated embodiment, the perforated undulating walls 1504 span the height "h" of the fluid flow channel 130 but are not so limited.

Figure 16:
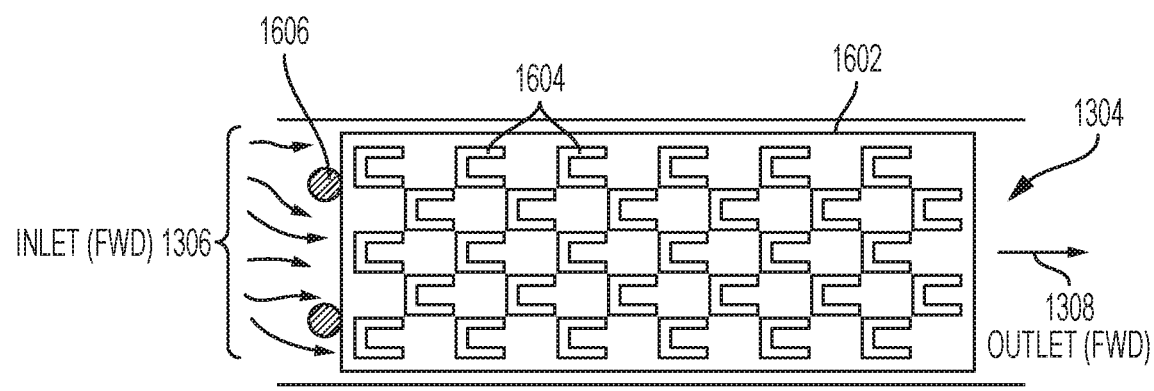
FIG. 16 shows a fourth exemplary surface profiling arrangement.

FIG. 16 shows a "shark fin" perforated sheet 1602 arrangement including a plurality of U-shaped protrusions 1604 which can have different orientations with respect to the flow of fluid from the inlet 1306 to the outlet 1308. In this embodiment, the perforated sheets 1602 can be locked in place with respect to the fluid flow channel 130 using pins 1606. Various orientations of the protrusions 1604 can be implemented so that flow in a delivery direction can be subject to high resistance (thus forming turbulent flow during drug delivery), while flow in the opposite direction (i.e., the filling direction) can be subject to relatively low resistance (thus achieving laminar flow during filling of the device).

Any of the fluid flow regulation arrangements, including any of the drug delivery systems and/or any of the fluid flow regulators disclosed herein, can be part of a wearable or on-body drug delivery device or pump, such as an Omni-Pod® (Insulet Corporation, Billerica, Mass., USA) device and/or any of the drug delivery devices described in U.S. Pat. Nos. 7,303,549; 7,144,384; 7,137,964; 6,960,192; 6,740,059; 6,699,218; 9,402,950; 7,771,412; 7,029,455; 6,740,05; and 6,656,159, each of which is incorporated herein by reference in its entirety.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

The invention claimed is:

1. A fluid regulating arrangement for dispensing a liquid drug, comprising:
   a liquid drug container configured to store a liquid drug;
   a compliance plate having a first opening, a second opening and a third opening, wherein the compliance plate is coupled on a first side to a first end of the liquid drug container;
   a flow channel selector plate having a central opening and coupled to a second side of the compliance plate; and
   a needle coupled to the central opening of the flow channel selector plate;
   wherein the first end of the liquid drug container comprises a first flow manifold and a second flow manifold, the first flow manifold having a first end in fluid communication with an interior of the liquid drug container, and a second end in fluid communication with the first opening of the compliance plate;
   wherein the flow channel selector plate is rotatable with respect to the compliance plate and the liquid drug container, the flow channel selector plate further having a fluid flow channel for receiving the liquid drug from the liquid drug container through the first flow manifold and the first opening of the compliance plate, and for directing the liquid drug out through the second opening of the compliance plate;
   wherein the second opening of the compliance plate is in fluid communication with the second flow manifold;
   wherein the second flow manifold is coupled to the third opening in the compliance plate for directing the liquid drug from the liquid drug container though the third opening and into fluid communication with the central opening of the flow channel selector plate and the needle; and
   rotating the flow channel selector plate exposes a different portion of the fluid flow channel between the first and second openings of the compliance plate to change a flow resistance of the liquid drug through the fluid flow channel.

2. The fluid regulating arrangement of claim 1, wherein the liquid drug container comprises a custom-shaped liquid drug container.

3. The fluid regulating arrangement of claim 1, wherein the liquid drug container comprises an International Organization for Standardization (ISO) glass cartridge.

4. The fluid regulating arrangement of claim 3, further comprising a cartridge adapter coupled to a mouth portion of the ISO glass cartridge.

5. The fluid regulating arrangement of claim 4, wherein the compliance plate and the flow channel selector plate are coupled to the cartridge adapter.

6. The fluid regulating arrangement of claim 5, wherein the cartridge adapter comprises one or more flexible snaps for coupling the cartridge adapter to the mouth portion of the ISO glass cartridge.

7. The fluid regulating arrangement of claim 1, wherein the fluid flow channel comprises a tapered cross-sectional flow profile.

8. The fluid regulating arrangement of claim 7, wherein the fluid flow channel comprises a semi-circular cross-sectional shape.

9. The fluid regulating arrangement of claim 7, wherein the fluid flow channel comprises a polygonal cross-sectional shape.

10. The fluid regulating arrangement of claim 1, wherein the fluid flow channel comprises a single channel arrangement.

11. The fluid regulating arrangement of claim 1, wherein the fluid flow channel comprises a double channel arrangement.

12. The fluid regulating arrangement of claim 11, wherein the double channel arrangement comprises a double tapered cross-sectional flow profile.

13. The fluid regulating arrangement of claim 11, wherein the double channel arrangement comprises a double stepped tapered cross-sectional flow profile.

14. The fluid regulating arrangement of claim 1, further comprising a plunger positioned in a second end of the liquid drug container.

15. The fluid regulating arrangement of claim 1, further comprising:
   a pressure sensor coupled to the needle to sense a flow rate of the liquid drug; and
   a motor coupled to the flow channel selector plate, wherein the motor adjusts a rotational position of the flow channel selector plate to adjust the flow resistance of the liquid drug through the fluid flow channel based on the sensed flow rate.

16. The fluid regulating arrangement of claim 1, further comprising a plurality of protrusions positioned on an interior surface of the fluid flow channel.

17. The fluid regulating arrangement of claim 1, wherein the third opening of the compliance plate is aligned with the central opening in the flow channel selector plate.

18. The fluid regulating arrangement of claim 1, wherein the compliance plate is stationary with respect to the flow channel selector plate and the flow channel selector plate is rotatable with respect to the stationary compliance plate and the liquid drug container.

* * * * *